(12) United States Patent
McAllister et al.

(10) Patent No.: US 9,957,567 B2
(45) Date of Patent: May 1, 2018

(54) METHODS RELATING TO DENND1A VARIANT 2 AND POLYCYSTIC OVARY SYNDROME

(71) Applicants: THE PENN STATE RESEARCH FOUNDATION, University Park, PA (US); VIRGINIA COMMONWEALTH UNIVERSITY, Richmond, VA (US)

(72) Inventors: Janette M McAllister, Hummelstown, PA (US); Jerome F Strauss, Richmond, VA (US)

(73) Assignees: VIRGINIA COMMONWEALTH UNIVERSITY, Richmond, VA (US); THE PENN STATE RESEARCH FOUNDATION, University Park, PA (US)

(*) Notice: Subject to any disclaimer, the term of this patent is extended or adjusted under 35 U.S.C. 154(b) by 583 days.

(21) Appl. No.: 14/402,134

(22) PCT Filed: Mar. 15, 2013

(86) PCT No.: PCT/US2013/031932
§ 371 (c)(1),
(2) Date: Nov. 19, 2014

(87) PCT Pub. No.: WO2013/176765
PCT Pub. Date: Nov. 28, 2013

(65) Prior Publication Data
US 2015/0087718 A1    Mar. 26, 2015

Related U.S. Application Data

(60) Provisional application No. 61/649,568, filed on May 21, 2012.

(51) Int. Cl.
C12Q 1/68       (2018.01)
G01N 33/561     (2006.01)

(52) U.S. Cl.
CPC ......... *C12Q 1/6883* (2013.01); *G01N 33/561* (2013.01); *C12Q 2600/112* (2013.01); *C12Q 2600/156* (2013.01)

(58) Field of Classification Search
CPC .................................................. C12Q 1/6883
See application file for complete search history.

(56) References Cited

U.S. PATENT DOCUMENTS

2009/0176235 A1    7/2009 Cargill et al.
2009/0220961 A1    9/2009 Liu et al.
(Continued)

FOREIGN PATENT DOCUMENTS

WO          0198353 A2    12/2001
WO    WO 2008067195 A2 *  6/2008    ........... C12Q 1/6883
WO          150545 A1    12/2011

OTHER PUBLICATIONS

Belouchi, A. et al. ATK90026, SEQ ID No. 651 (Nov. 13, 2008), Alignment of SEQ ID No. 1 with SEQ ID No. 651.*
(Continued)

*Primary Examiner* — Diana B Johannsen
(74) *Attorney, Agent, or Firm* — Whitham, Curtis & Cook, P.C.

(57) ABSTRACT

Provided are compositions and methods for use in polycystic ovary syndrome diagnosis (PCOS). The method involves a sample from a subject for a DENND1A Variant 2 mRNA or DENND1 A Variant 2 protein to make or aid in a diagnosis of PCOS. Also provided are methods for selecting an individual as a candidate for therapy for polycystic ovary syndrome by testing a biological sample from an individual for DENND1 A Variant 2 mRNA or DENND1 A Variant 2 protein and designating the individual as a candidate for the
(Continued)

PCOS based on determining DENND1 A Variant 2 mRNA or DENND1 A Variant 2 protein in the sample. Also provided are products for use in aiding diagnosis of PCOS which contain reagents for detecting DENND1 A Variant 2 mRNA or DENND1 A Variant 2 protein, and packaging containing printed material describing use and indications for the product.

14 Claims, 7 Drawing Sheets

(56) References Cited

U.S. PATENT DOCUMENTS

2009/0221437 A1   9/2009   Harkin et al.
2011/0003704 A1   1/2011   Skog et al.

OTHER PUBLICATIONS

Goodarzi et al. "Replication of association of DENND1A and THADA variants with polycystic ovary syndrome in European cohorts," Journal of Medical Genetics, Dec. 17, 2011, pp. 90-95, vol. 49.
Welt et al. "Variants in DENND1A are Associated with Polycystic Ovary Syndrome in Women of European Ancestry," The Journal of Clinical Endocrinology & Metabolism, Apr. 30, 2012, pp. E1342-E1347, vol. 97.

\* cited by examiner

B

C

SEQUENCE LISTING

<160> NUMBER OF SEQ ID NOS: 27

<210> SEQ ID NO 1
<211> LENGTH: 2166
<212> TYPE: DNA
<213> ORGANISM: Homo sapiens

<400> SEQUENCE: 1

```
cgcgcgccgg gcacgcgcgc cggcgaccat ggcgttcgcc gggctggagc gagtacatta      60 accccctggag gcggcggcgg cggcgaggga gcgagcctcg agcgggcggg ccccagcctg     120
agggaaggga ggaaggggcg gggagagcgc cagagggagg ccggtcggcc gcgggcgggc     180
gggcagcgca gcgccgagcg gggcccgcgg gcccatgagg aggcctgggg accatgggct     240
ccaggatcaa gcagaatcca gagaccacat ttgaagtata tgttgaagtg gcctatccca     300
ggacaggtgg cactctttca gatcctgagg tgcagaggca attcccggag gactacagtg     360
accaggaagt tctacagact ttgaccaagt tttgtttccc cttctatgtg gacagcctca     420
cagttagcca agttggccag aacttcacat tcgtgctcac tgacattgac agcaaacaga     480
gattcgggtt ctgccgctta tcttcaggag cgaagagctg cttctgtatc ttaagctatc     540
tcccctggtt cgaggtattt tataagctgc ttaacatcct ggcagattac acgacaaaaa     600
gacaggaaaa tcagtggaat gagcttcttg aaactctgca caaacttccc atccctgacc     660
caggagtgtc tgtccatctc agcgtgcatt cttattttac tgtgcctgat accagagaac     720
ttcccagcat acctgagaat agaaatctga cagaatattt tgtggctgtg gatgttaaca     780
acatgttgca tctgtacgcc agtatgctgt acgaacgccg gatactcatc atttgcagca     840
aactcagcac tctgactgcc tgcatccacg ggtctgcggc gatgctctac cccatgtact     900
ggcagcacgt gtacatcccc gtgctgccgc cgcatctgct ggactactgc tgtgctccca     960
tgccctacct cataggaatc catttaagtt taatggagaa agtcagaaac atggccctgg    1020
atgatgtcgt gatcctgaat gtggacacca cacccctgga aaccccttc gatgacctcc     1080 agagcctccc aaacgacgtg atctcttccc tgaagaacag gctgaaaaag gtctccacaa    1140
ccactgggga tggtgtggcc agagcgttcc tcaaggccca ggctgctttc ttcggtagct    1200
accgaaacgc tctgaaaatc gagccggagg agccgatcac tttctgtgag gaagccttcg    1260
```

```
tgtcccacta ccgctccgga gccatgaggc agttcctgca gaacgccaca cagctgcagc    1320
tcttcaagca gtttattgat ggtcgattag atcttctcaa ttccggcgaa ggtttcagtg    1380 atgttttga agaggaaatc aacatgggcg agtacgctgg cagtgacaaa ctgtaccatc    1440
agtggctctc cactgtccgg aaaggaagtg gagcaattct gaatactgta aagaccaaag    1500
caaatccggc catgaagact gtctacaagt tcgcaaaaga tcatgcaaaa atgggaataa    1560
aagaggtgaa aaaccgcttg aagcaaaagg acattgccga gatggctgc gcccccaccc    1620 cagaagagca gctgccaaag actgcaccgt ccccactggt ggaggccaag gaccccaagc    1680
tccgagaaga ccggcggcca atcacagtcc actttggaca ggtgcgccca cctcgtccac    1740
atgttgttaa gagaccaaag agcaacatcg cagtggaagg ccggaggacg tctgtgccga    1800
gccctgagca aaacaccatt gcaacaccag ctacactcca catcctacag aaaagcatta    1860
cccattttgc ggccaagttc ccgacgagag gctggacctc ttcatcacat tgacttacgc    1920
cgttgctttt ccagactggg cagaggggct gacttcgcag tgtgtgccaa agagccggtg    1980
tctgataatc ccattttcct gcttatcacc tgaactgtgt cagtatcact tttagttttg    2040
ttggttggtt ggtttgttgt ttgtttaata tgccctgttt tctacttctg ttggaaaata    2100
tttggggttg aaataaacca gtgggagcat ggaaaaaaaa aaaaaaaaaa aaaaaaaaa    2160 aaaaaa                                                               2166
```

<210> SEQ ID NO 2
<211> LENGTH: 559
<212> TYPE: PRT
<213> ORGANISM: Homo sapiens

<400> SEQUENCE: 2

```
Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val His Ser Tyr Phe Thr Val Pro Asp Thr
145                 150                 155                 160

Arg Glu Leu Pro Ser Ile Pro Glu Asn Arg Asn Leu Thr Glu Tyr Phe
                165                 170                 175

Val Ala Val Asp Val Asn Asn Met Leu His Leu Tyr Ala Ser Met Leu
            180                 185                 190

Tyr Glu Arg Arg Ile Leu Ile Ile Cys Ser Lys Leu Ser Thr Leu Thr
        195                 200                 205
```

Ala Cys Ile His Gly Ser Ala Ala Met Leu Tyr Pro Met Tyr Trp Gln
210                 215                 220

His Val Tyr Ile Pro Val Leu Pro Pro His Leu Leu Asp Tyr Cys Cys
225                 230                 235                 240

Ala Pro Met Pro Tyr Leu Ile Gly Ile His Leu Ser Leu Met Glu Lys
            245                 250                 255

Val Arg Asn Met Ala Leu Asp Asp Val Val Ile Leu Asn Val Asp Thr
                260                 265                 270

Asn Thr Leu Glu Thr Pro Phe Asp Asp Leu Gln Ser Leu Pro Asn Asp
            275                 280                 285

Val Ile Ser Ser Leu Lys Asn Arg Leu Lys Val Ser Thr Thr Thr
290                 295                 300

Gly Asp Gly Val Ala Arg Ala Phe Leu Lys Ala Gln Ala Ala Phe Phe
305                 310                 315                 320

Gly Ser Tyr Arg Asn Ala Leu Lys Ile Glu Pro Glu Pro Ile Thr
            325                 330                 335

Phe Cys Glu Glu Ala Phe Val Ser His Tyr Arg Ser Gly Ala Met Arg
                340                 345                 350

Gln Phe Leu Gln Asn Ala Thr Gln Leu Gln Leu Phe Lys Gln Phe Ile
            355                 360                 365

Asp Gly Arg Leu Asp Leu Leu Asn Ser Gly Glu Gly Phe Ser Asp Val
            370                 375                 380

Phe Glu Glu Glu Ile Asn Met Gly Glu Tyr Ala Gly Ser Asp Lys Leu
385                 390                 395                 400

Tyr His Gln Trp Leu Ser Thr Val Arg Lys Gly Ser Gly Ala Ile Leu
                405                 410                 415

Asn Thr Val Lys Thr Lys Ala Asn Pro Ala Met Lys Thr Val Tyr Lys
            420                 425                 430

Phe Ala Lys Asp His Ala Lys Met Gly Ile Lys Glu Val Lys Asn Arg
            435                 440                 445

Leu Lys Gln Lys Asp Ile Ala Glu Asn Gly Cys Ala Pro Thr Pro Glu
450                 455                 460

Glu Gln Leu Pro Lys Thr Ala Pro Ser Pro Leu Val Glu Ala Lys Asp
465                 470                 475                 480

Pro Lys Leu Arg Glu Asp Arg Arg Pro Ile Thr Val His Phe Gly Gln
                485                 490                 495

Val Arg Pro Pro Arg Pro His Val Val Lys Arg Pro Lys Ser Asn Ile
                500                 505                 510

Ala Val Glu Gly Arg Arg Thr Ser Val Pro Ser Pro Glu Gln Asn Thr
            515                 520                 525

Ile Ala Thr Pro Ala Thr Leu His Ile Leu Gln Lys Ser Ile Thr His
            530                 535                 540

Phe Ala Ala Lys Phe Pro Thr Arg Gly Trp Thr Ser Ser Ser His
545                 550                 555

<210> SEQ ID NO 3
<211> LENGTH: 5041
<212> TYPE: DNA
<213> ORGANISM: Homo sapiens

<400> SEQUENCE: 3
cgcgcgccgg gcacgcgcgc cggcgaccat ggcgttcgcc gggctggagc gagtacatta      60 accccctggag gcggcggcgg cggcgaggga gcgagcctcg agcgggcggg ccccagcctg    120

-continued

| | |
|---|---|
| agggaaggga ggaaggggcg gggagagcgc cagagggagg ccggtcggcc gcgggcgggc | 180 |
| gggcagcgca gcgccgagcg gggcccgcgg gcccatgagg aggcctgggg accatgggct | 240 |
| ccaggatcaa gcagaatcca gagaccacat ttgaagtata tgttgaagtg gcctatccca | 300 |
| ggacaggtgg cactctttca gatcctgagg tgcagaggca attcccggag gactacagtg | 360 |
| accaggaagt tctacagact tgaccaagt ttttgtttccc cttctatgtg gacagcctca | 420 |
| cagttagcca agttggccag aacttcacat tcgtgctcac tgacattgac agcaaacaga | 480 |
| gattcgggtt ctgccgctta tcttcaggag cgaagagctg cttctgtatc ttaagctatc | 540 |
| tccccctggtt cgaggtattt tataagctgc ttaacatcct ggcagattac acgacaaaaa | 600 |
| gacaggaaaa tcagtggaat gagcttcttg aaactctgca caaacttccc atccctgacc | 660 |
| caggagtgtc tgtccatctc agcgtgcatt cttattttac tgtgcctgat accagagaac | 720 |
| ttcccagcat acctgagaat agaaatctga cagaatattt tgtggctgtg gatgttaaca | 780 |
| acatgttgca tctgtacgcc agtatgctgt acgaacgccg gatactcatc atttgcagca | 840 |
| aactcagcac tctgactgcc tgcatccacg ggtctgcggc gatgctctac cccatgtact | 900 |
| ggcagcacgt gtacatcccc gtgctgccgc cgcatctgct ggactactgc tgtgctccca | 960 |
| tgccctacct cataggaatc catttaagtt taatggagaa agtcagaaac atggccctgg | 1020 |
| atgatgtcgt gatcctgaat gtggacacca cacccctgga aaccccccttc gatgacctcc | 1080 |
| agagcctccc aaacgacgtg atctcttccc tgaagaacag gctgaaaaag gtctccacaa | 1140 |
| ccactgggga tggtgtggcc agagcgttcc tcaaggccca ggctgctttc ttcggtagct | 1200 |
| accgaaacgc tctgaaaatc gagccggagg agccgatcac tttctgtgag gaagccttcg | 1260 |
| tgtcccacta ccgctccgga gccatgaggc agttcctgca gaacgccaca cagctgcagc | 1320 |
| tcttcaagca gtttattgat ggtcgattag atcttctcaa ttccggcgaa ggtttcagtg | 1380 |
| atgttttttga agaggaaatc aacatgggcg agtacgctgg cagtgacaaa ctgtaccatc | 1440 |
| agtggctctc cactgtccgg aaaggaagtg gagcaattct gaatactgta aagaccaaag | 1500 |
| caaatccggc catgaagact gtctacaagt cgcaaaagaa tcatgcaaaa atgggaataa | 1560 |
| aagaggtgaa aaaccgcttg aagcaaaagg acattgccga gaatggctgc gcccccaccc | 1620 |
| cagaagagca gctgccaaag actgcaccgt ccccactggt ggaggccaag gaccccaagc | 1680 |
| tccgagaaga ccggcggcca atcacagtcc actttggaca ggtgcgccca cctcgtccac | 1740 |
| atgttgttaa gagaccaaag agcaacatcg cagtggaagg ccggaggacg tctgtgccga | 1800 |
| gccctgagca gccgcagccg tatcggacac tcagggagtc agacagcgcg gaaggcgacg | 1860 |
| aggcagagag tccagagcag caagtgcgga agtccacagg ccctgtccca gctcccccctg | 1920 |
| accgggctgc cagcatcgac cttctggaag acgtcttcag caacctggac atggaggccg | 1980 |
| cactgcagcc actgggccag gccaagagct tagaggacct tcgtgccccc aaagacctga | 2040 |
| gggagcagcc agggacctttt gactatcaga ggctggatct gggcgggagt gagaggagcc | 2100 |
| gcggggtgac agtggccttg aagcttaccc acccgtacaa caagctctgg agcctgggcc | 2160 |
| aggacgacat ggccatcccc agcaagcccc cagctgcctc ccctgagaag ccctcggccc | 2220 |
| tgctcggaaa ctccctggcc ctgcctcgaa ggccccagaa ccgggacagc atcctgaacc | 2280 |
| ccagtgacaa ggaggaggtg cccaccccta ctctgggcag catcaccatc ccccggcccc | 2340 |
| aaggcaggaa gaccccagag ctgggcatcg tgcctccacc gcccattccc gcccggcca | 2400 |
| agctccaggc tgccggcgcc gcacttggtg acgtctcaga gcggctgcag acggatcggg | 2460 |
| acaggcgagc tgccctgagt ccagggctcc tgcctggtgt tgtccccaa ggccccactg | 2520 |

```
aactgctcca gccgctcagc cctggccccg gggctgcagg cacgagcagt gacgccctgc    2580 tcgcccctcct ggacccgctc agcacagcct ggtcaggcag caccctcccg tcacgccccg    2640
ccaccccgaa tgtagccacc ccattcaccc cccaattcag cttccccct gcagggacac     2700 ccaccccatt cccacagcca ccactcaacc cctttgtccc atccatgcca gcagcccac     2760 ccaccctgcc cctggtctcc acaccagccg ggcctttcgg ggcccctcca gcttccctgg    2820
ggccggcttt tgcgtccggc ctcctgctgt ccagtgctgg cttctgtgcc cctcacaggt    2880
ctcagcccaa cctctccgcc ctctccatgc ccaacctctt tggccagatg cccatgggca    2940
cccacacgag cccctacag ccgctgggtc cccagcagt tgcccgtcg aggatccgaa       3000 cgttgcccct ggcccgctca agtgccaggg ctgctgagac caagcagggg ctggccctga    3060
ggcctggaga cccccgctt ctgcctccca ggcccctca aggcctggag ccaacactgc      3120
agccctctgc tcctcaacag gccagagacc cctttgagga tttgttacag aaaaccaagc   3180
aagacgtgag cccgagtccg gccctggccc cggcccaga ctcggtggag cagctcagga    3240
agcagtggga gaccttcgag tgagccgggc cctgagggtg gggatgcac cgaggcccga    3300 gggtccgtcc actgctgcgg ttccgaggct ccccgccac tctctctctg cccaggttct    3360
gctggtggga agggatggga cccctctctg ctgcccccctc ctccctcca cactgcccat   3420 ctctgatgtc tggccctggg gaatggcacc agttccagcc tgggaatcaa cccagttcct   3480
gagtgcccat cccaccccgc ggttgcctct cctcggcacc cttgattggg ttttgcacta    3540
aagaggtcag ctgggccaat gatattgctc cagaccgagt cctacccacc ttcccccgga    3600
agtgtcccaa gaggctccga aggcctcccc tccgagccca gctctcctgt ctcctccaca    3660
gccaggccct gcacgcccac ctcctcggac acaggtgaca gggttaccct ccagtttgag    3720
ctcatctgca cgagacacag gtagcttggg gttgaagtta ggactcctcc tgggctggag    3780
gatttacctg gtggggcact tccagactgt ttctagcaat atacacacac gttctttcct    3840
gtgtcttcac cccaaaactt cagttgattc tgacctggga ggatctgggg accaggggt    3900 cttgggctgc cttgtgatac acagccccag ccaccctgca cggggggctgc gagcaccagc   3960 aactttgatt tatagaagga aaatggaaac ccccatctga gtattttggg aggagccccc    4020
agccctcatc cagctctggc acgctgatac ctccaggtac tcccctcact gtcaaagctg    4080
gggctcagcc tcttgtcatc tggagctttg tgggcaaagc tgagaagctg caacccagat    4140
ttcaacccaa aaaggtcaag ctgaatgcct cagactgatg tggaaggcag ctggccttcc    4200
tgggttggaa cgaggcagtg gccctgagcc ccttctccag ggcaggtag aaaggacaaa     4260 cttggtctct gcctcgggga agcaggagga gggctagaag ccagtccctc cccacctgcc    4320
cagagctcca ggcagcaca gaaattcctg aggccaacgt caccaaagtt agattgaatg     4380
tttattatct ttcttttttcc ttttttacctt attgatttga tgaatcttga aatggattca    4440
tttccataaa ccaagttaaa gtatggcccg accattttaag aaaacaacca tctgagacac   4500
gcaggaaatt gtgagcattt cgacccgagc tctcatttcc tatttgtgaa gggtcagaca    4560
cagtctaccc aggggtgtct ggggacaag ggggtctctg gagatgtcac ccagggagcc    4620
ccctctatgt ctgagaggct gccactgctg cacatgctca gtgaggcttg gcggccatcc    4680
tggcacatgg ctcttcctgg gtcaaccgtg acctgtctgg ctcaggaatg ggctctggct    4740 gctggggag ccgtgtcact cctgggccat ggggcacct cctgggcact taggtgtttc       4800
agcatagatt ccagtttcgc accctgggca gaccccagg cccatccgg gatagggcag      4860
```

-continued

```
aggaggtgct ggcggcccca gggaaggagg gtgtgtaccc caaggccccc tggctgtgct    4920
gaggggctgg ggtgagcgct ccatgttcac atgagcactg ctgcctcttc acttgtggga    4980 cttttttgcaa acccaaggat gaactttgtg tgcattcaat aaaatcatct tggggaagag    5040
g                                                                    5041

<210> SEQ ID NO 4
<211> LENGTH: 1009
<212> TYPE: PRT
<213> ORGANISM: Homo sapiens

<400> SEQUENCE: 4

Met Gly Ser Arg Ile Lys Gln Asn Pro Glu Thr Thr Phe Glu Val Tyr
1               5                   10                  15

Val Glu Val Ala Tyr Pro Arg Thr Gly Gly Thr Leu Ser Asp Pro Glu
            20                  25                  30

Val Gln Arg Gln Phe Pro Glu Asp Tyr Ser Asp Gln Glu Val Leu Gln
        35                  40                  45

Thr Leu Thr Lys Phe Cys Phe Pro Phe Tyr Val Asp Ser Leu Thr Val
    50                  55                  60

Ser Gln Val Gly Gln Asn Phe Thr Phe Val Leu Thr Asp Ile Asp Ser
65                  70                  75                  80

Lys Gln Arg Phe Gly Phe Cys Arg Leu Ser Ser Gly Ala Lys Ser Cys
                85                  90                  95

Phe Cys Ile Leu Ser Tyr Leu Pro Trp Phe Glu Val Phe Tyr Lys Leu
            100                 105                 110

Leu Asn Ile Leu Ala Asp Tyr Thr Thr Lys Arg Gln Glu Asn Gln Trp
        115                 120                 125

Asn Glu Leu Leu Glu Thr Leu His Lys Leu Pro Ile Pro Asp Pro Gly
    130                 135                 140

Val Ser Val His Leu Ser Val His Ser Tyr Phe Thr Val Pro Asp Thr
145                 150                 155                 160

Arg Glu Leu Pro Ser Ile Pro Glu Asn Arg Asn Leu Thr Glu Tyr Phe
                165                 170                 175

Val Ala Val Asp Val Asn Asn Met Leu His Leu Tyr Ala Ser Met Leu
            180                 185                 190

Tyr Glu Arg Arg Ile Leu Ile Ile Cys Ser Lys Leu Ser Thr Leu Thr
        195                 200                 205

Ala Cys Ile His Gly Ser Ala Ala Met Leu Tyr Pro Met Tyr Trp Gln
    210                 215                 220

His Val Tyr Ile Pro Val Leu Pro Pro His Leu Leu Asp Tyr Cys Cys
225                 230                 235                 240

Ala Pro Met Pro Tyr Leu Ile Gly Ile His Leu Ser Leu Met Glu Lys
                245                 250                 255

Val Arg Asn Met Ala Leu Asp Asp Val Val Ile Leu Asn Val Asp Thr
            260                 265                 270

Asn Thr Leu Glu Thr Pro Phe Asp Asp Leu Gln Ser Leu Pro Asn Asp
        275                 280                 285

Val Ile Ser Ser Leu Lys Asn Arg Leu Lys Lys Val Ser Thr Thr Thr
    290                 295                 300

Gly Asp Gly Val Ala Arg Ala Phe Leu Lys Ala Gln Ala Ala Phe Phe
305                 310                 315                 320

Gly Ser Tyr Arg Asn Ala Leu Lys Ile Glu Pro Glu Glu Pro Ile Thr
                325                 330                 335
```

-continued

Phe Cys Glu Glu Ala Phe Val Ser His Tyr Arg Ser Gly Ala Met Arg
            340                 345                 350

Gln Phe Leu Gln Asn Ala Thr Gln Leu Gln Leu Phe Lys Gln Phe Ile
        355                 360                 365

Asp Gly Arg Leu Asp Leu Leu Asn Ser Gly Glu Gly Phe Ser Asp Val
    370                 375                 380

Phe Glu Glu Glu Ile Asn Met Gly Glu Tyr Ala Gly Ser Asp Lys Leu
385                 390                 395                 400

Tyr His Gln Trp Leu Ser Thr Val Arg Lys Gly Ser Gly Ala Ile Leu
                405                 410                 415

Asn Thr Val Lys Thr Lys Ala Asn Pro Ala Met Lys Thr Val Tyr Lys
            420                 425                 430

Phe Ala Lys Asp His Ala Lys Met Gly Ile Lys Glu Val Lys Asn Arg
        435                 440                 445

Leu Lys Gln Lys Asp Ile Ala Glu Asn Gly Cys Ala Pro Thr Pro Glu
    450                 455                 460

Glu Gln Leu Pro Lys Thr Ala Pro Ser Pro Leu Val Glu Ala Lys Asp
465                 470                 475                 480

Pro Lys Leu Arg Glu Asp Arg Pro Ile Thr Val His Phe Gly Gln
                485                 490                 495

Val Arg Pro Pro Arg Pro His Val Val Lys Arg Pro Lys Ser Asn Ile
            500                 505                 510

Ala Val Glu Gly Arg Arg Thr Ser Val Pro Ser Pro Glu Gln Pro Gln
        515                 520                 525

Pro Tyr Arg Thr Leu Arg Glu Ser Asp Ser Ala Glu Gly Asp Glu Ala
    530                 535                 540

Glu Ser Pro Glu Gln Gln Val Arg Lys Ser Thr Gly Pro Val Pro Ala
545                 550                 555                 560

Pro Pro Asp Arg Ala Ala Ser Ile Asp Leu Leu Glu Asp Val Phe Ser
                565                 570                 575

Asn Leu Asp Met Glu Ala Ala Leu Gln Pro Leu Gly Gln Ala Lys Ser
            580                 585                 590

Leu Glu Asp Leu Arg Ala Pro Lys Asp Leu Arg Glu Gln Pro Gly Thr
        595                 600                 605

Phe Asp Tyr Gln Arg Leu Asp Leu Gly Gly Ser Glu Arg Ser Arg Gly
    610                 615                 620

Val Thr Val Ala Leu Lys Leu Thr His Pro Tyr Asn Lys Leu Trp Ser
625                 630                 635                 640

Leu Gly Gln Asp Asp Met Ala Ile Pro Ser Lys Pro Pro Ala Ala Ser
                645                 650                 655

Pro Glu Lys Pro Ser Ala Leu Leu Gly Asn Ser Leu Ala Leu Pro Arg
            660                 665                 670

Arg Pro Gln Asn Arg Asp Ser Ile Leu Asn Pro Ser Asp Lys Glu Glu
        675                 680                 685

Val Pro Thr Pro Thr Leu Gly Ser Ile Thr Ile Pro Arg Pro Gln Gly
    690                 695                 700

Arg Lys Thr Pro Glu Leu Gly Ile Val Pro Pro Pro Ile Pro Arg
705                 710                 715                 720

Pro Ala Lys Leu Gln Ala Gly Ala Ala Leu Gly Asp Val Ser Glu
                725                 730                 735

Arg Leu Gln Thr Asp Arg Asp Arg Arg Ala Ala Leu Ser Pro Gly Leu
            740                 745                 750

Leu Pro Gly Val Val Pro Gln Gly Pro Thr Glu Leu Leu Gln Pro Leu

```
                  755                 760                 765
Ser Pro Gly Pro Gly Ala Ala Gly Thr Ser Ser Asp Ala Leu Leu Ala
            770                 775                 780
Leu Leu Asp Pro Leu Ser Thr Ala Trp Ser Gly Ser Thr Leu Pro Ser
785                 790                 795                 800
Arg Pro Ala Thr Pro Asn Val Ala Thr Pro Phe Thr Pro Gln Phe Ser
                805                 810                 815
Phe Pro Pro Ala Gly Thr Pro Thr Pro Phe Pro Gln Pro Pro Leu Asn
            820                 825                 830
Pro Phe Val Pro Ser Met Pro Ala Ala Pro Thr Leu Pro Leu Val
                835                 840                 845
Ser Thr Pro Ala Gly Pro Phe Gly Ala Pro Ala Ser Leu Gly Pro
            850                 855                 860
Ala Phe Ala Ser Gly Leu Leu Ser Ser Ala Gly Phe Cys Ala Pro
865                 870                 875                 880
His Arg Ser Gln Pro Asn Leu Ser Ala Leu Ser Met Pro Asn Leu Phe
                885                 890                 895
Gly Gln Met Pro Met Gly Thr His Thr Ser Pro Leu Gln Pro Leu Gly
            900                 905                 910
Pro Pro Ala Val Ala Pro Ser Arg Ile Arg Thr Leu Pro Leu Ala Arg
                915                 920                 925
Ser Ser Ala Arg Ala Ala Glu Thr Lys Gln Gly Leu Ala Leu Arg Pro
            930                 935                 940
Gly Asp Pro Pro Leu Leu Pro Pro Arg Pro Gln Gly Leu Glu Pro
945                 950                 955                 960
Thr Leu Gln Pro Ser Ala Pro Gln Gln Ala Arg Asp Pro Phe Glu Asp
                965                 970                 975
Leu Leu Gln Lys Thr Lys Gln Asp Val Ser Pro Ser Pro Ala Leu Ala
            980                 985                 990
Pro Ala Pro Asp Ser Val Glu Gln Leu Arg Lys Gln Trp Glu Thr Phe
            995                1000                1005
Glu

<210> SEQ ID NO 5
<211> LENGTH: 356
<212> TYPE: DNA
<213> ORGANISM: Homo sapiens

<400> SEQUENCE: 5
aaacaccatt gcaacaccag ctacactcca catcctacag aaaagcatta cccattttgc       60
ggccaagttc ccgacgagag gctggacctc ttcatcacat tgacttacgc cgttgctttt      120
ccagactggg cagaggggct gacttcgcag tgtgtgccaa agagccggtg tctgataatc      180 ccatttttcct gcttatcacc tgaactgtgt cagtatcact tttagttttg ttggttggtt     240
ggtttgttgt tgtttaata tgccctgttt tctacttctg ttggaaaata tttgggttg        300 aaataaacca gtgggagcat ggaaaaaaaa aaaaaaaaa aaaaaaaaaa aaaaaa            356

<210> SEQ ID NO 6
<211> LENGTH: 322
<212> TYPE: DNA
<213> ORGANISM: Homo sapiens

<400> SEQUENCE: 6
aaacaccatt gcaacaccag ctacactcca catcctacag aaaagcatta cccattttgc       60
```

```
ggccaagttc cgacgagag gctggacctc ttcatcacat tgacttacgc cgttgctttt    120
ccagactggg cagaggggct gacttcgcag tgtgtgccaa agagccggtg tctgataatc    180 ccatttcct gcttatcacc tgaactgtgt cagtatcact tttagttttg ttggttggtt    240
ggtttgttgt ttgtttaata tgccctgttt tctacttctg ttggaaaata tttggggttg    300
aaataaacca gtgggagcat gg                                             322

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
gggctgactt cgcagtgtgt                                                 20

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
acagttcagg tgataagcag gaaa                                            24

<210> SEQ ID NO 9
<211> LENGTH: 28
<212> TYPE: DNA
<213> ORGANISM: Artificial Sequence
<220> FEATURE:
<223> OTHER INFORMATION: Artificial sequence
<220> FEATURE:
<221> NAME/KEY: misc_feature
<223> OTHER INFORMATION: n is a secondary quenching moiety
<220> FEATURE:
<221> NAME/KEY: misc_feature
<222> LOCATION: (10)..(10)
<223> OTHER INFORMATION: n is a, c, g, or t

<400> SEQUENCE: 9
ccaaagagcn cggtgtctga taatccca                                        28

<210> SEQ ID NO 10
<211> LENGTH: 33
<212> TYPE: PRT
<213> ORGANISM: Homo sapiens

<400> SEQUENCE: 10

Asn Thr Ile Ala Thr Pro Ala Thr Leu His Ile Leu Gln Lys Ser Ile
1               5                   10                  15

Thr His Phe Ala Ala Lys Phe Pro Thr Arg Gly Trp Thr Ser Ser
            20                  25                  30

His

<210> SEQ ID NO 11
<211> LENGTH: 21
<212> TYPE: PRT
<213> ORGANISM: Homo sapiens

<400> SEQUENCE: 11

Gln Lys Ser Ile Thr His Phe Ala Ala Lys Phe Pro Thr Arg Gly Trp
1               5                   10                  15
```

Thr Ser Ser Ser His
            20

<210> SEQ ID NO 12
<211> LENGTH: 23
<212> TYPE: DNA
<213> ORGANISM: Artificial Sequence
<220> FEATURE:
<223> OTHER INFORMATION: Artificial sequence

<400> SEQUENCE: 12
cgacgagagg ctggacctct tac                                           23

<210> SEQ ID NO 13
<211> LENGTH: 23
<212> TYPE: DNA
<213> ORGANISM: Artificial Sequence
<220> FEATURE:
<223> OTHER INFORMATION: Artificial sequence

<400> SEQUENCE: 13
cctcttcatc acattgactt acg                                           23

<210> SEQ ID NO 14
<211> LENGTH: 19
<212> TYPE: DNA
<213> ORGANISM: Artificial Sequence
<220> FEATURE:
<223> OTHER INFORMATION: Artificial sequence

<400> SEQUENCE: 14
ctcttcatca cattgactt                                                19

<210> SEQ ID NO 15
<211> LENGTH: 212
<212> TYPE: DNA
<213> ORGANISM: Artificial Sequence
<220> FEATURE:
<223> OTHER INFORMATION: Artificial sequence

<400> SEQUENCE: 15
cgttgctttt ccagactggg cagaggggct gacttcgcag tgtgtgccaa agagccggtg    60
tctgataatc ccattttcct gcttatcacc tgaactgtgt cagtatcact tttagttttg   120
ttggttggtt ggtttgttgt ttgtttaata tgccctgttt tctacttctg ttggaaaata   180
tttggggttg aaataaacca gtgggagcat gg                                 212

<210> SEQ ID NO 16
<211> LENGTH: 27
<212> TYPE: DNA
<213> ORGANISM: Artificial Sequence
<220> FEATURE:
<223> OTHER INFORMATION: Synthetic primer

<400> SEQUENCE: 16
ggattcattt ccataaacca agttaaa                                       27

<210> SEQ ID NO 17
<211> LENGTH: 21
<212> TYPE: DNA
<213> ORGANISM: Artificial Sequence
<220> FEATURE:
<223> OTHER INFORMATION: Synthetic primer

<400> SEQUENCE: 17
cacaatttcc tgcgtgtctc a                                               21

<210> SEQ ID NO 18
<211> LENGTH: 30
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore or secondary quenching
      moiety
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 18
natggcccga nccatttaag aaaacaacca                                      30

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
ggcctcaaat ggcaactcta ga                                              22

<210> SEQ ID NO 20
<211> LENGTH: 21
<212> TYPE: DNA
<213> ORGANISM: Artificial Sequence
<220> FEATURE:
<223> OTHER INFORMATION: Synthetic primer

<400> SEQUENCE: 20
cttctgatcg ccatccttga a                                               21

<210> SEQ ID NO 21
<211> LENGTH: 27
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore
<220> FEATURE:
<221> NAME/KEY: misc_feature
<222> LOCATION: (1)..(1)
<223> OTHER INFORMATION: n is a, c, g, or t

<400> SEQUENCE: 21
ntcgcgtcca acaaccgtaa gggtatc                                         27

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22

-continued

```
cacggcactg attttcagtt c                                         21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
tcttgctgcc agtctggact                                           20

<210> SEQ ID NO 24
<211> LENGTH: 26
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore
<220> FEATURE:
<221> NAME/KEY: misc_feature
<222> LOCATION: (1)..(1)
<223> OTHER INFORMATION: n is a, c, g, or t

<400> SEQUENCE: 24
ntgtgcacag gagccaagag tgaaga                                    26

<210> SEQ ID NO 25
<211> LENGTH: 22
<212> TYPE: DNA
<213> ORGANISM: Artificial Sequence
<220> FEATURE:
<223> OTHER INFORMATION: Synthetic primer

<400> SEQUENCE: 25
gtctcccatc caagtactaa cc                                        22

<210> SEQ ID NO 26
<211> LENGTH: 28
<212> TYPE: DNA
<213> ORGANISM: Artificial Sequence
<220> FEATURE:
<223> OTHER INFORMATION: Synthetic probe
<220> FEATURE:
<221> NAME/KEY: misc_feature
<223> OTHER INFORMATION: n is a fluorophore or secondary quenching
      moiety
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 26
ntctcgtctg natctcggaa gctaagca                                  28

<210> SEQ ID NO 27
<211> LENGTH: 50
<212> TYPE: PRT
<213> ORGANISM: Artificial Sequence
<220> FEATURE:
<223> OTHER INFORMATION: Synthetic sequence

<400> SEQUENCE: 27
```

-continued

```
Pro Gly Val Ser Val His Leu Ser Val His Ser Tyr Phe Thr Val Pro
1               5                   10                  15

Asp Thr Arg Glu Leu Pro Ser Ile Pro Glu Asn Arg Asn Leu Thr Glu
            20                  25                  30

Tyr Phe Val Ala Val Asp Val Asn Asn Met Leu His Leu Tyr Ala Ser
        35                  40                  45

Met Leu
    50
```

METHODS RELATING TO DENND1A VARIANT 2 AND POLYCYSTIC OVARY SYNDROME

CROSS REFERENCE TO RELATED APPLICATIONS

This application claims priority to U.S. Provisional application No. 61/649,568, filed on May 21, 2012, the disclosure of which is incorporated herein by reference.

STATEMENT REGARDING FEDERALLY SPONSORED RESEARCH

This invention was made with government support under Grant Nos. HD033852, HD034449, and HD058300, awarded by the National Institutes of Health. The Government has certain rights in the invention.

FIELD OF THE INVENTION

The present invention relates generally to polycystic ovary syndrome (PCOS) and more specifically to compositions and methods for detection and diagnosis of PCOS.

BACKGROUND OF THE INVENTION

PCOS is the most common endocrine disturbance of women of reproductive age, affecting approximately 6-10% of women in this population, and is a common cause of infertility. PCOS has a similar incidence among ethnic and racial groups.

PCOS is characterized by traits that include but are not necessarily limited to abnormal accumulation of small follicles within the ovary, oligomenorrhea or amenorrhea, acne, *Acanthosis nigricans*, male pattern alopecia, increased ovarian androgen production, infertility/first trimester miscarriage, hirsutism, hyperinsulinemia/insulin resistance and obesity. Clinical criteria for PCOS include hyperandrogenemia, increased total testosterone and/or bioavailable testosterone, oligo-ovulation, polycystic ovaries and fewer than six periods/year. When attempting to definitively diagnose PCOS, other causes of these symptoms (e.g., tumors secreting androgens, congenital adrenal hyperplasia, Cushing's syndrome) need to be excluded.

Currently, diagnosis of PCOS is complex and frequently involves testing of hormone levels to rule out late-onset congenital adrenal hyperplasia (LOCAH) or non-classical adrenal hyperplasia (NCAH), and Cushing's syndrome. Testing frequently performed includes measurements of Testosterone, Dehydroepiandrosterone sulfate (DHEAS), 17α-Hydroxyprogesterone, Sex hormone-binding globulin (SHBG), prolactin levels, thyroid function tests, and transvaginal ultrasound to assess ovarian morphology. Thus, there remains a longstanding need for improved compositions and methods that can be used in connection with PCOS diagnosis, for monitoring therapeutic/surgical interventions, and for selecting patients for personalized therapeutic approaches. The present invention meets these and other needs.

SUMMARY OF THE INVENTION

The present invention provides compositions and methods for making or for aiding in making a diagnosis of PCOS. In general, the method comprises detection and/or quantitation of DENND1A Variant 2 mRNA or DENND1A Variant 2 protein in a sample obtained or derived from a subject.

The invention is suitable for testing samples from any human individual, including females and males of any age, regardless of medical condition. Thus, in various embodiments, the invention provides method a that can be used for convenient and rapid determination of the presence and/or amount of DENND1A Variant 2 mRNA and/or protein in a wide variety of biological samples, non-limiting examples of which are described further below. The invention is expected to provide earlier, easier and more definitive diagnosis of PCOS than what has heretofore been available. In certain embodiments, the invention permits testing of any biological sample, including but not limited to any tissue or biological fluids, non-limiting examples of which include blood, urine, plasma, serum, or mucosal fluid, including saliva. The invention includes testing of samples which contain exosomes, such as a sample of blood, urine, or saliva which contains or would be expected to contain exosomes. In certain embodiments, the invention is performed on a sample that is non-invasively obtained from the subject.

Detection of the DENND1A Variant 2 mRNA and/or protein can be performed using any method. In various embodiments, the mRNA is detected using a polymerase chain reaction (PCR)-based approach, such as real time (RT)-PCR. In alternative approaches, DENND1A Variant 2 mRNA is detected by hybridization of a labeled probe, whereby the hybridized labeled probe is detected. As such, the method is amenable to being performed as part of a multiplexed assay, such as on a chip or an array. In alternative embodiments, the DENND1A Variant 2 protein is detected. Detection/quantitation of the DENND1A Variant 2 protein can be performed using, for example, any immunological-based detection mechanism. In various approaches, detecting the DENND1A Variant 2 protein is performed using either polyclonal or monoclonal antibodies so that a complex comprising DENND1A Variant 2 protein and the antibodies is detected.

In another aspect, the invention provides a method for selecting an individual as a candidate for therapy for PCOS. This involves testing a sample from an individual for DENND1A Variant 2 mRNA and/or DENND1A Variant 2 protein, and subsequent to detecting/quantitating the DENND1A Variant 2 mRNA or protein in the sample, designating the individual as a candidate for the PCOS therapy (or not so designating, if the sample does not contain DENND1A Variant 2 mRNA or protein, or contains less of either as compared to a reference). In certain embodiments, the method involves treating the individual for PCOS subsequent to detecting/quantitating the DENND1A Variant 2 mRNA or protein in a sample from the individual.

The invention also provides a product for use in making or aiding diagnosis of PCOS. The product can comprise reagents, such as probes and/or primers, wherein at least one of the probes and/or the primers can specifically hybridize to DENND1A Variant 2 mRNA. The product can additionally contain packaging, and printed material indicating that the product is to be used to detect DENND1A Variant 2 mRNA as an indicator of PCOS. The printed material can include instructions as to how the reagents provided as part of the product are to be used to make or aid a PCOS diagnosis.

BRIEF DESCRIPTION OF THE FIGURES

FIG. 1A shows that CYP17 mRNA accumulation was significantly increased in PCOS theca cells as compared to normal theca cells treated under basal and forskolin stimulated conditions (*, P<0.05). FIG. 1B shows that DHEA biosynthesis in PCOS theca cells was significantly increased under both basal and forskolin stimulated conditions (*, P<0.05).

FIG. 3A shows that DENND1A Variant 1 is not differentially expressed in normal and PCOS theca cells. In contrast, DENND1A Variant 2 mRNA accumulation was significantly increased under both basal (*, P<0.01) and forskolin (, P<0.05) stimulated conditions in PCOS theca cells, as compared to normal cells.

FIG. 5A depicts a representative Western Blot analysis which shows increased 62 kD DENND1A Variant 2 (DENND1A.V2) in PCOS theca cells. FIG. 5B shows that the 62 kD DENND1A Variant 2 was present in the nuclear component of PCOS theca cells, but the 110 kD DENND1A Variant 1 was not detected in normal or PCOS whole cell or nuclear extracts. These data demonstrate that DENND1A Variant 2 protein is present in the nucleus, and may traffic from the cell membrane where DENND1A proteins are thought to associate with clathrin to the nucleus to regulate a variety of cell functions in the ovarian theca cell.

FIG. 6A shows that all doses of DENND1A.V2 adenovirus significantly increased forskolin-stimulated DHEA production compared with control Null (empty) adenovirus (*, P<0.05). FIG. 6B shows that infection of normal theca cells with 3.0 pfu of adenovirus expressing DENND1A.V2 results in a significant increase in forskolin-stimulated DHEA biosynthesis compared to empty virus infected cells (*, P<0.05). FIG. 6C shows that both 1.0 and 10 pfu DENND1A.V2 adenovirus significantly increased CYP17 mRNA accumulation in normal cells, with and without forskolin stimulation, as compared to infection with Null adenovirus (*, P<0.05). FIG. 6D shows that DENND1A.V2 adenovirus increases both basal (*, P<0.05). and forskolin-stimulated (**, P<0.01). -770 CYP17A1 promoter activity as compared to Null adenovirus.

As shown in FIG. 7A, DENND1A.V2 shRNA1 and shRNA2 retrovirus plasmid significantly inhibited both basal (*, P<0.05) and forskolin (*, P<0.01) stimulated CYP17 mRNA accumulation in PCOS theca cells. As shown in FIG. 7B, co-transfection of −235/+44 of the CYP17A1 promoter fused to the luciferase gene in a pGL3 plasmid with DENND1A.V2 shRNA1 and shRNA2 resulted in a significant inhibition of forskolin-dependent CYP17A1 reporter activity in PCOS theca cells, compared to Scrambled shRNA (*, P<0.05). To evaluate the effect of knockdown of DENND1A.V2 on DHEA biosynthesis, PCOS theca cells were infected with a silencing shRNA DENND1A.V2 lentivirus or a control non-silencing lentivirus in the presence or absence of forskolin for 72 h. As shown in FIG. 7C, infection with silencing shRNA DENND1A.V2 lentivirus significantly inhibited forskolin-stimulated DHEA biosynthesis (*, P<0.05).

As shown in FIG. 8A, DENND1A.V2 significantly increased both basal and LH/hCG-stimulated DHEA biosynthesis (*, P<0.05). As shown in FIG. 8B, DENND1A.V2 significantly increased LH/hCG-stimulated CYP17A1 promoter function (*, P<0.05).

DETAILED DESCRIPTION OF THE INVENTION

Figure 1:
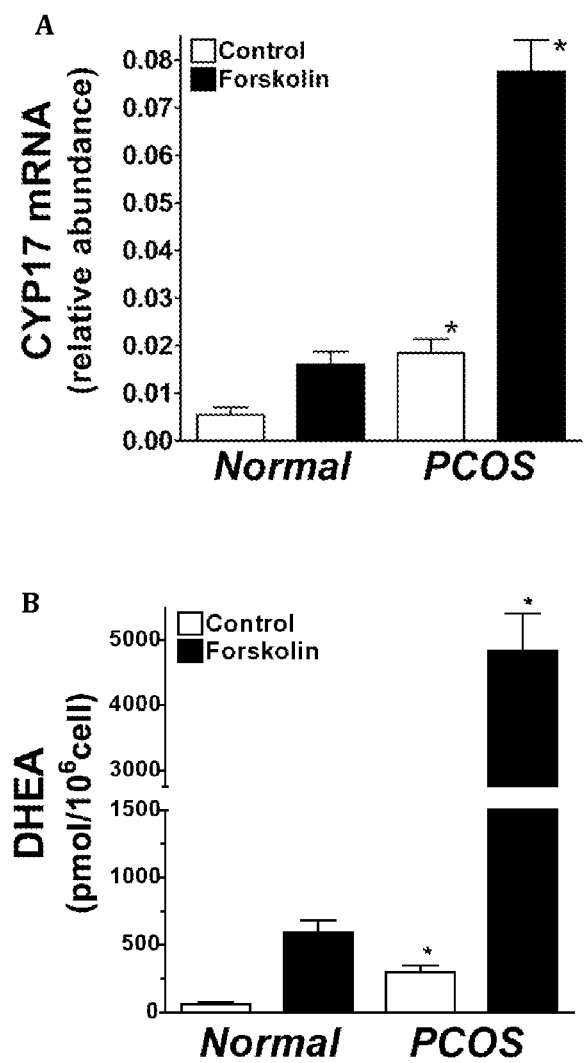
FIGS. 1A and 1B provide graphical summaries of data which together demonstrate that both basal and cAMP-stimulated CYP17 mRNA accumulation and DHEA production are increased in PCOS theca cells propagated in long-term culture.

The present invention provides compositions and methods that are useful for, among other purposes, diagnosis of PCOS or any other condition that is positively correlated with expression of the DENND1A Variant 2 mRNA and/or protein, as further described herein. The invention is also suitable for determining whether or not an individual is a candidate for PCOS therapy, for development of a treatment regime for an individual who is diagnosed with PCOS, and for monitoring PCOS therapy.

The method generally comprises testing a sample for the presence or absence of DENND1A Variant 2 mRNA or protein, or for comparing an amount of DENND1A Variant 2 mRNA or protein to a reference. In embodiments of the invention, determining the presence of DENND1A Variant 2 mRNA or protein aids in the diagnoses of a condition that is positively correlated with DENND1A Variant 2 expression. In one embodiment, determining the presence of DENND1A Variant 2 mRNA or protein is considered a diagnosis of PCOS.

The DENND1A Variant 1 and DENND1A Variant 2 are also referred to as the "DENND1A isoform 1" and "DENND1A isoform 2" respectively, and as "DENND1A.V1" and "DENND1A.V2", respectively.

The DENND1A Variant 2 cDNA sequence is: (SEQ ID NO:1):

```
                                        (SEQ ID NO: 1)
0001    cgcgcgccgg gcacgcgcgc cggcgaccat ggcgttcgcc
        gggctggagc gagtacatta 0061    acccctggag gcggcggcgg cggcgaggga gcgagcctcg
        agcgggcggg ccccagcctg 0121    agggaaggga ggaaggggcg gggagagcgc cagagggagg
        ccggtcggcc gcggcgggc 0181    gggcagcgca gcgccgagcg gggcccgcgg gcccatgagg
        aggcctgggg accatgggct 0241    ccaggatcaa gcagaatcca gagaccacat ttgaagtata
        tgttgaagtg gcctatccca 0301    ggacaggtgg cactctttca gatcctgagg tgcagaggca
        attcccggag gactacagtg 0361    accaggaagt tctacagact ttgaccaagt tttgtttccc
        cttctatgtg gacagcctca 0421    cagttagcca agttggccag aacttcacat tcgtgctcac
        tgacattgac agcaaacaga 0481    gattcgggtt ctgccgctta tcttcaggag cgaagagctg
        cttctgtatc ttaagctatc 0541    tcccctggtt cgaggtattt tataagctgc ttaacatcct
        ggcagattac acgacaaaaa 0601    gacaggaaaa tcagtggaat gagcttcttg aaactctgca
        caaacttccc atccctgacc 0661    caggagtgtc tgtccatctc agcgtgcatt cttatttac
        tgtgcctgat accagagaac 0721    ttcccagcat acctgagaat agaaatctga cagaatattt
        tgtggctgtg gatgttaaca 0781    acatgttgca tctgtacgcc agtatgctgt acgaacgccg
        gatactcatc atttgcagca 0841    aactcagcac tctgactgcc tgcatccacg ggtctgcggc
        gatgctctac cccatgtact 0901    ggcagcacgt gtacatcccc gtgctgccgc cgcatctgct
        ggactactgc tgtgctccca 0961    tgccctacct cataggaatc catttaagtt aatggagaa
        agtcagaaac atggcctgg 1021    atgatgtcgt gatcctgaat gtggacacca caccctgga
        aaccccttc gatgacctcc 1081    agagcctccc aaacgacgtg atctcttccc tgaagaacag
        gctgaaaaag gtctccacaa 1141    ccactgggga tggtgtggcc agagcgttcc tcaaggccca
        ggctgctttc ttcggtagct 1201    accgaaacgc tctgaaaatc gagccggagg agccgatcac
        tttctgtgag gaagccttcg 1261    tgtcccacta ccgctccgga gccatgaggc agttcctgca
        gaacgccaca cagctgcagc 1321    tcttcaagca gtttattgat ggtcgattag atcttctcaa
        ttccggcgaa ggtttcagtg 1381    atgttttga gaggaaatc aacatgggcg agtacgctgg
        cagtgacaaa ctgtaccatc 1441    agtggctctc cactgtccgg aaaggaagtg gagcaattct
        gaatactgta aagaccaaag
```

-continued

```
1501    caaatccggc catgaagact gtctacaagt tcgcaaaaga
        tcatgcaaaa atgggaataa 1561    aagaggtgaa aaaccgcttg aagcaaaagg acattgccga
        gaatggctgc gcccccaccc 1621    cagaagagca gctgccaaag actgcaccgt ccccactggt
        ggaggccaag gaccccaagc 1681    tccgagaaga ccggcggcca atcacagtcc actttggaca
        ggtgcgccca cctcgtccac 1741    atgttgttaa agaccaaag agcaacatcg cagtggaagg
        ccggaggacg tctgtgccga 1801    gccctgcaga aacaccatt gcaacaccag ctacactcca
        catcctacag aaaagcatta 1861    cccattttgc ggccaagttc ccgacgagag gctggacctc
        ttcatcacat tgacttacgc 1921    cgttgctttt ccagactggg cagaggggct gacttcgcag
        tgtgtgccaa agagccggtg 1981    tctgataatc ccattttcct gcttatcacc tgaactgtgt
        cagtatcact tttagttttg 2041    ttggttggtt ggtttgttgt ttgtttaata tgccctgttt
        tctacttctg ttggaaaata 2101    tttggggttg aaataaacca gtgggagcat ggaaaaaaaa
        aaaaaaaaaa aaaaaaaaa 2161    aaaaaa
```

The DENND1A Variant 2 amino acid sequence is (SEQ ID NO:2):

```
                                        (SEQ ID NO: 2)
MGSRIKQNPETTFEVYVEVAYPRTGGTLSDPEVQRQFPEDYSDQEVL

QTLTKFCFPFYVDSLTVSQVGQNFTFVLTDIDSKQRFGFCRLSSGAK

SCFCILSYLPWEEVEYKLLNILADYTTKRQENQWNELLETLHKLPIP

DPGVSVHLSVHSYFTVPDTRELPSIPENRNLTEYFVAVDVNNMLHLY

ASMLYERRILIICSKLSTLTACIHGSAAMLYPMYWQHVYIPVLPPHL

LDYCCAPMPYLIGIHLSLMEKVRNMALDDVVILNVDTNTLETPFDDL

QSLPNDVISSLKNRLKKVSTTTGDGVARAFLKAQAAFFGSYRNALKI

EPEEPITFCEEAFVSHYRSGAMRQFLQNATQLQLFKQFIDGRLDLLN

SGEGESDVFEEEINMGEYAGSDKLYHQWLSTVRKGSGAILNTVKTKA

NPAMKTVYKFAKDHAKMGIKEVKNRLKQKDIAENGCAPTPEEQLPKT

APSPLVEAKDPKLREDRRPITVHFGQVRPPRPHVVKRPKSNIAVEGR

RTSVPSPEQNTIATPATLHILQKSITHFAAKEPTRGWTSSSH
```

The DENND1A Variant 1 cDNA sequence is (SEQ ID NO:3):

```
                                        (SEQ ID NO: 3)
0001    cgcgcgccgg gcacgcgcgc cggcgaccat ggcgttcgcc
        gggctggagc gagtacatta 0061    acccctggag gcggcggcgg cggcgaggga gcgagcctcg
        agcgggcggg ccccagcctg 0121    agggaaggga ggaaggggcg gggagagcgc cagagggagg
        ccggtcggcc gcggcgggc 0181    gggcagcgca gcgccgagcg gggcccgcgg gcccatgagg
        aggcctgggg accatgggct
```

```
0241  ccaggatcaa gcagaatcca gagaccacat ttgaagtata
      tgttgaagtg gcctatccca
0301  ggacaggtgg cactctttca gatcctgagg tgcagaggca
      attcccggag gactacagtg
0361  accaggaagt tctacagact ttgaccaagt tttgtttccc
      cttctatgtg gacagcctca
0421  cagttagcca agttggccag aacttcacat tcgtgctcac
      tgacattgac agcaaacaga
0481  gattcgggtt ctgccgctta tcttcaggag cgaagagctg
      cttctgtatc ttaagctatc
0541  tccctggtt cgaggtattt tataagctgc ttaacatcct
      ggcagattac acgacaaaaa
0601  gacaggaaaa tcagtggaat gagcttcttg aaactctgca
      caaacttccc atccctgacc
0661  caggagtgtc tgtccatctc agcgtgcatt cttattttac
      tgtgcctgat accagagaac
0721  ttcccagcat acctgagaat agaaatctga cagaatattt
      tgtggctgtg gatgttaaca
0781  acatgttgca tctgtacgcc agtatgctgt acgaacgccg
      gatactcatc atttgcagca
0841  aactcagcac tctgactgcc tgcatccacg ggtctgcggc
      gatgctctac cccatgtact
0901  ggcagcacgt gtacatcccc gtgctgccgc cgcatctgct
      ggactactgc tgtgctccca
0961  tgccctacct cataggaatc catttaagtt taatggagaa
      agtcagaaac atggccctgg
1021  atgatgtcgt gatcctgaat gtggacacca acaccctgga
      aaccccttc gatgacctcc
1081  agagcctccc aaacgacgtg atctcttccc tgaagaacag
      gctgaaaaag gtctccacaa
1141  ccactgggga tggtgtggcc agagcgttcc tcaaggccca
      ggctgctttc ttcggtagct
1201  accgaaacgc tctgaaaatc gagccggagg agccgatcac
      tttctgtgag gaagccttcg
1261  tgtcccacta ccgctccgga gccatgaggc agttcctgca
      gaacgccaca cagctgcagc
1321  tcttcaagca gtttattgat ggtcgattag atcttctcaa
      ttccggcgaa ggtttcagtg
1381  atgttttga agaggaaatc aacatgggcg agtacgctgg
      cagtgacaaa ctgtaccatc
1441  agtggctctc cactgtccgg aaaggaagtg gagcaattct
      gaatactgta aagaccaaag
1501  caaatccggc catgaagact gtctacaagt tcgcaaaaga
      tcatgcaaaa atggaataa
1561  aagaggtgaa aaaccgcttg aagcaaaagg acattgccga
      gaatggctgc gcccccaccc
1621  cagaagagca gctgccaaag actgcaccgt ccccactggt
      ggaggccaag gaccccaagc
1681  tccgagaaga ccggcggcca atcacagtcc actttggaca
      ggtgcgccca cctcgtccac
1741  atgttgttaa gagaccaaag agcaacatcg cagtggaagg
      ccggaggacg tctgtgccga
1801  gccctgagca gccgcagccg tatcggacac tcagggagtc
      agacagcgcg gaaggcgacg
1861  aggcagagag tccagagcag caagtgcgga agtccacagg
      ccctgtccca gctcccctg
1921  accgggctgc cagcatcgac cttctggaag acgtcttcag
      caacctggac atggaggccg
1981  cactgcagcc actgggccag gccaagagct tagaggacct
      tcgtgccccc aaagacctga
2041  gggagcagcc agggaccttt gactatcaga ggctggatct
      gggcgggagt gagaggagcc
2101  gcggggtgac agtggccttg aagcttaccc acccgtacaa
      caagctctgg agcctgggcc
2161  aggacgacat ggccatcccc agcaagcccc agctgcctc
      ccctgagaag ccctcggccc
2221  tgctcgggaa ctccctggcc ctgcctcgaa ggccccagaa
      ccgggacagc atcctgaacc
2281  ccagtgacaa ggaggaggtg cccacccta ctctgggcag
      catcaccatc ccccggcccc
2341  aaggcaggaa gaccccagag ctgggcatcg tgcctccacc
      gcccattccc cgcccggcca
2401  agctccaggc tgccggcgcc gcacttggtg acgtctcaga
      gcggctgcag acggatcggg
2461  acaggcgagc tgccctgagt ccagggctcc tgcctggtgt
      tgtcccccaa ggccccactg
2521  aactgctcca gccgctcagc cctggccccg gggctgcagg
      cacgagcagt gacgccctgc
2581  tcgcctcct ggaccgctc agcacagcct ggtcaggcag
      cacccctccccg tcacgccccg
2641  ccaccccgaa tgtagccacc ccattcaccc cccaattcag
      cttccccct gcagggacac
2701  ccaccccatt cccacagcca ccactcaacc cctttgtccc
      atccatgcca gcagcccac
2761  ccaccctgcc cctggtctcc acaccagccg ggccttcgg
      ggcccctcca gcttccctgg
2821  ggccggcttt tgcgtccggc ctcctgctgt ccagtgctgg
      cttctgtgcc cctcacaggt
2881  ctcagcccaa cctctccgcc ctctccatgc ccaacctctt
      tggccagatg cccatgggca
2941  cccacacgag cccctacag ccgctgggtc ccccagcagt
      tgccccgtcg aggatccgaa
3001  cgttgccct ggcccgctca gtgccaggg ctgctgagac
      caagcagggg ctggccctga
3061  ggcctggaga ccccccgctt ctgcctccca ggcccctca
      aggcctggag ccaacactgc
3121  agccctctgc tcctcaacag gccagagacc cctttgagga
      tttgttacag aaaaccaagc
3181  aagacgtgag cccgagtccg gccctggccc cggccccaga
      ctcggtggag cagctcagga
3241  agcagtggga gaccttcgag tgagccgggc cctgagggtg
      ggggatgcac cgaggcccga
3301  gggtccgtcc actgctgcgg ttccgaggct ccccgccac
      tctctctctg cccaggttct
3361  gctggtggga agggatggga cccctctctg ctgccccctc
      ctcccctcca cactgcccat
3421  ctctgatgtc tggccctggg gaatggcacc agttccagcc
      tgggaatcaa cccagttcct
```

```
3481 gagtgcccat cccacccgc ggttgcctct cctcggcacc
     cttgattggg ttttgcacta
3541 aagaggtcag ctgggccaat gatattgctc cagaccgagt
     cctacccacc ttccccccgga
3601 agtgtcccaa gaggctccga aggcctcccc tccgagccca
     gctctcctgt ctcctccaca
3661 gccaggccct gcacgcccac ctcctcggac acaggtgaca
     gggttaccct ccagtttgag
3721 ctcatctgca cgagacacag gtagcttggg gttgaagtta
     ggactcctcc tgggctggag
3781 gatttacctg gtggggcact tccagactgt ttctagcaat
     atacacacac gttctttcct
3841 gtgtcttcac cccaaaactt cagttgattc tgacctggga
     ggatctgggg accagggggt
3901 cttgggctgc cttgtgatac acagcccag ccaccctgca
     cgggggctgc gagcaccagc
3961 aactttgatt tatagaagga aaatggaaac ccccatctga
     gtattttggg aggagccccc
4021 agccctcatc cagctctggc acgctgatac ctccaggtac
     tcccctcact gtcaaagctg
4081 gggctcagcc tcttgtcatc tggagctttg tgggcaaagc
     tgagaagctg caacccagat
4141 ttcaacccaa aaaggtcaag ctgaatgcct cagactgatg
     tggaaggcag ctggccttcc
4201 tgggttgaa cgaggcagtg gccctgagcc ccttctccag
     ggccaggtag aaaggacaaa
4261 cttggtctct gcctcgggga agcaggagga gggctagaag
     ccagtccctc cccacctgcc
4321 cagagctcca ggccagcaca gaaattcctg aggccaacgt
     caccaaagtt agattgaatg
4381 tttattatct ttcttttcc tttttacctt attgatttga
     tgaatcttga aatggattca
4441 tttccataaa ccaagttaaa gtatggcccg accatttaag
     aaaacaacca tctgagacac
4501 gcaggaaatt gtgagcattt cgacccgagc tctcatttcc
     tatttgtgaa gggtcagaca
4561 cagtctaccc aggggtgtct gggggacaag ggggtctctg
     gagatgtcac ccagggagcc
4621 ccctctatgt ctgagaggct gccactgctg cacatgctca
     gtgaggcttg gcggccatcc
4681 tggcacatgg ctcttcctgg gtcaaccgtg acctgtctgg
     ctcaggaatg ggctctggct
4741 gctggggag ccgtgtcact cctgggccat gggggcacct
     cctgggcact taggtgtttc
4801 agcatagatt ccagtttcgc accctgggca gaccccagg
     ccccatccgg gataggggag
4861 aggaggtgct ggcggcccca gggaaggagg gtgtgtaccc
     caaggccccc tggctgtgct
4921 gaggggctgg ggtgagcgct ccatgttcac atgagcactg
     ctgcctcttc acttgtggga
4981 cttttgcaa acccaaggat gaactttgtg tgcattcaat
     aaaatcatct tggggaagag
5041 g
```

The DENND1A Variant 1 amino acid sequence is (SEQ ID NO:4):

(SEQ ID NO: 4)
MGSRIKQNPETTFEVYVEVAYPRTGGTLSDPEVQRQFPEDYSDQEVL
QTLTKFCFPPFYVDSLTVSQVGQNFTFVLTDIDSKQRFGFCRLSSGAK
SCFCILSYLPWEEVEYKLLNILADYTTKRQENQWNELLETLHKLPIP
DPGVSVHLSVHSYFTVPDTRELPSIPENRNLTEYFVAVDVNNMLHLY
ASMLYERRILIICSKLSTLTACIHGSAAMLYPMYWQHVYIPVLPPHL
LDYCCAPMPYLIGIHLSLMEKVRNMALDDVVILNVDTNTLETPFDDL
QSLPNDVISSLKNRLKKVSTTTGDGVARAFLKAQAAFFGSYRNALKI
EPEEPITFCEEAFVSHYRSGAMRQFLQNATQLQLFKQFIDGRLDLLN
SGEGESDVFEEEINMGEYAGSDKLYHQWLSTVRKGSGAILNTVKTKA
NPAMKTVYKFAKDHAKMGIKEVKNRLKQKDIAENGCAPTPEEQLPKT
APSPLVEAKDPKLREDRRPITVHFGQVRPPRPHVVKRPKSNIAVEGR
RTSVPSPEQPQPYRTLRESDSAEGDEAESPEQQVRKSTGPVPAPPDR
AASIDLLEDVFSNLDMEAALQPLGQAKSLEDLRAPKDLREQPGTFDY
QRLDLGGSERSRGVTVALKLTHPYNKLWSLGQDDMAIPSKPPAASPE
KPSALLGNSLALPRRPQNRDSILNPSDKEEVPTPTLGSITIPRPQGR
KTPELGIVPPPPIPRPAKLQAAGAALGDVSERLQTDRDRRAALSPGL
LPGVVPQGPTELLQPLSPGPGAAGTSSDALLALLDPLSTAWSGSTLP
SRPATPNVATPFTPQFSFPPAGTPTPFPQPPLNPFVPSMPAAPPTLP
LVSTPAGPFGAPPASLGPAFASGLLLSSAGFCAPHRSQPNLSALSMP
NLFGQMPMGTHTSPLQPLGPPAVAPSRIRTLPLARSSARAAETKQGL
ALRPGDPPLLPPRPPQGLEPTLQPSAPQQARDPFEDLLQKTKQDVSP
SPALAPAPDSVEQLRKQWETFE

For each cDNA sequence presented herein, the invention includes the mRNA equivalent of the cDNA, meaning that the invention includes each cDNA sequence wherein each T is replaced by U. In embodiments, determining polynucleotides comprising or consisting of the cDNA sequence or segments thereof is considered to be the same as determining the corresponding mRNA.

Our experiments indicate that DENND1A.V2 is central to the pathogenesis of PCOS because of its role in controlling cell signaling, making it a strong biomarker of the disease. The present invention includes but is not limited to the novel finding that DENND1A Variant 2 mRNA and protein is increased in PCOS ovarian theca cells, as well as in other tissues, including but not necessarily limited to urine exosomes. Accordingly, it is demonstrated herein that increased DENND1A Variant 2 is a characteristic of PCOS and can be used as a diagnostic marker for PCOS. In furtherance of determining the relationship between DENND1A Variant 2 and PCOS, we present data that show that the presence of DENND1A Variant 2 results in an increase in ovarian androgen production, as well as increased CYP17A1 gene expression, the latter due to increased transcription driven from the CYP17A1 promoter. We also demonstrate that transfection of ovarian theca cells with DENND1A Variant 2 results in decreased LKB1 and ERK phosphorylation, which are associated with conversion of normal cells to a PCOS phenotype. Thus, it is likely that DENND1A Variant 2 acts as an upstream signaling component which can affect down-stream signaling events, including but not necessarily limited to acting on Mitogen-activated protein kinase (MAPK) and LKB1/5' adenosine monophosphate-activated protein kinase (AMPK) signaling pathways. It is believed this results in increased androgen production consistent with that observed in PCOS. Data presented herein also demonstrate that targeted blockage of DENND1A Variant 2 by RNAi-mediated mRNA degradation can inhibit the deleterious effects of DENND1A Variant 2, at least in respect of its effect on CYP17A1 expression, thereby further confirming its role as a diagnostic marker, and that it likely plays a material role in the etiology of PCOS. These results also implicate DENND1A Variant 2 as a target for therapeutic intervention.

While the present invention is amenable to testing a wide variety of biological samples, we notably demonstrate that DENND1A Variant 2 mRNA can be detected in urine exosomal RNA, and thus can be expected to be detectable in any other biological sample, including but not limited to biological fluids. Accordingly, in certain embodiments, the invention provides a non-invasive approach for detecting DENND1A Variant 2 in samples obtained from any human subject. Thus, the invention permits testing from any individual, regardless of age, gender, overall health or disease condition. This is a particular concern when considering the diagnosis in adolescents or pubertal children where non-invasive testing would provide great value. The invention thus includes in various aspects tools for use in a convenient and rapid approach for determining the presence and/or amount of DENND1A Variant 2 in a wide variety of biological samples, illustrative embodiments of which are described further below. These tools are expected to facilitate earlier, easier and more definitive diagnosis of PCOS than previously available approaches.

The biological sample tested according to the invention can be any biological sample that contains or would be suspected to contain nucleic acids and/or protein. The sample can be a tissue sample, or a sample of a biological liquid. Non-limiting examples of tissues include samples obtained by way of biopsy, such as a biopsy of ovarian tissue, or a sample of mucosa. The sample can be a sample comprising theca cells. In other non-limiting examples, the sample can be a liquid sample such as blood, urine, plasma, serum, or mucosal fluid, including saliva. In certain embodiments, the sample comprises exosomes, such as a sample of blood or urine which contains or would be expected to contain exosomes. In other embodiments, the sample can be a sample of reproductive tissue, or exudate such as ovarian exudate or endometrial tissue or exudate. In a preferred embodiment, the sample is one that is non-invasively obtained from the subject, such as a sample comprising urine, a mucosal sample, or a sample of oral fluid, such as saliva or sputum.

In certain approaches, the sample is obtained from the subject and used directly in determining the presence or absence or amount of the DENND1A Variant 2. In other embodiments, the biological sample is obtained and subjected to a processing step before the biological sample is used in testing for the DENND1A Variant 2. In some examples, the processing step can be carried out to isolate, and/or purify and/or amplify the DENND1A Variant 2 mRNA, or to isolate and/or purify the DENND1A Variant 2 protein.

In certain embodiments, the invention is useful for testing a sample from an pre-pubescent or adolescent human female. In certain examples, the female can be as young as eight years old. In certain embodiments the sample is from a human female that is younger that eight years old, such as an infant. In other embodiments, the invention is useful for testing a sample obtained from a human male. In this regard, it is expected that determining DENND1A Variant 2 mRNA or protein in a sample obtained from a human male will be useful because we suspect there is involvement of DENND1A Variant 2 in certain conditions in human males, such as metabolic disorders that comprise conditions affecting lipid metabolism, including but not limited to hyperlipidemias and cardiovascular conditions related to lipid metabolism. In one embodiment, the subject tested according to the invention is a human male who has a female sibling who has been diagnosed with PCOS.

Suitable techniques for determining the presence or absence or quantitating DENND1A Variant 2 mRNA include but are not limited to hybridization of probes or primers directed to DENND1A Variant 2 mRNA, or by using various chip technologies, polynucleotide or oligonucleotide arrays, and combinations thereof. Thus, in various embodiments, probes to the DENND1A Variant 2 mRNA or a DNA equivalent of it can be arranged and/or fixed on a solid support.

DENND1A Variant 2 mRNA may be tested directly or may be amplified enzymatically in vitro by, for example, use of the polymerase chain reaction (PCR), Real-Time (RT) PCR, including quantitative real-time (QT-RT) PCR analysis, or any other in vitro amplification methods. For amplification reactions, primers can be designed which hybridize to DENND1A Variant 2 mRNA, and used to obtain nucleic acid amplification products (i.e., amplicons). Those skilled in the art will recognize how to design suitable primers and perform amplification and/or hybridization reactions in order to carry out various embodiments of the method of the invention. In general, the primers should be long enough to be useful in amplification reactions, and generally primers which are at least 12 bases in length are considered suitable for such purposes, but primers as short as 8 bases can be used depending on reaction conditions. The primers/probes used for detecting DENND1A Variant 2 RNA can comprise modifications, such as being conjugated to one or more detectable labels, such as fluorophores in the form of a reporter dye and/or a quenching moiety for use in reactions such as real time (RT)-PCR, which allow quantitation of DNA amplified from RNA, wherein the quantitation can be performed over time concurrent with the amplification. In one embodiment, the amplification reaction comprises at least one polynucleotide probe specific for DENND1A Variant 2 mRNA, wherein the probe includes one terminal nucleotide modified to include a fluorescent tag, and the other terminal nucleotide modified to comprise a moiety that quenches fluorescence from the fluorescent tag. For instance, for use in RT-PCR, such a probe can be designed so that it binds with specificity to a portion of DENNDA1 Variant 2 or its complement that is between and does not overlap sequences to which two RT-PCR primers hybridize. Using this design, signal from the fluorescent tag will be quenched until the probe is degraded via exonuclease activity of the polymerase during amplification, at which point the fluorescent nucleotide will be separated from the quenching moiety and its signal will be detectable.

It will be recognized by those skilled in the art that while particular sequences of primers are provided herein, other primer sequences can be designed to detect the DENND1A Variant 2 mRNA. In certain embodiments, at least two synthetic oligonucleotide primers are used in an amplification reaction. The primers in different embodiments can be from 8 to 100 nucleotides in length, inclusive, and including all integers there between. The primers are of sufficient length and nucleotide composition to specifically hybridize under stringent conditions to DENND1A Variant 2 mRNA, and to cDNA equivalents thereof. In non-limiting examples, a first synthetic primer for use in an amplification reaction comprises or consists of a polynucleotide sequence that is identical to at least 8 contiguous nucleotides in the Variant 2 mRNA sequence, and a second primer comprises or consists of a polynucleotide sequence that is complementary to at least 8 contiguous nucleotides in the Variant 2 mRNA sequence. Longer primers can tolerate a certain number of mismatched nucleotides that will be apparent to one skilled in the art, and are dictated by such well known parameters as melting temperature and stringency. The primers can be designed such that they do not have complementarity to one another. In one embodiment, the primers are designed to amplify the following segment of the Variant 2 mRNA sequence, which comprises a 3'-mRNA sequence of DENND1A Variant 2 that is different than the DENND1A mRNA Variant 1 sequence. This distinct 3' segment includes a stop codon and a frameshift resulting in a shorter mRNA and distinct carboxy-terminal 33 amino acid sequence in DENND1A Variant 2. The message comprises a stop codon ending at nt1913 and an untranslated sequence beginning at nt1914. The mRNA of DENDA1A Variant two has mRNA coding sequence that is distinct from DENND1A Variant 1 from 1811-1913. The sequence of the 3'-region shown is the cDNA equivalent of the DENND1A Variant 2 mRNA segment, as indicated by the nucleotide positions:

```
                                              (SEQ ID NO: 5)
1811            aaacaccatt gcaacaccag ctacactcca
     catcctacag aaaagcatta 1861 cccattttgc ggccaagttc ccgacgagag gctggacctc
     ttcatcacat tgacttacgc 1921 cgttgctttt ccagactggg cagaggggct gacttcgcag
     tgtgtgccaa agagccggtg 1981 tctgataatc ccattttcct gcttatcacc tgaactgtgt
     cagtatcact tttagttttg 2041 ttggttggtt ggtttgttgt ttgtttaata tgccctgttt
     tctacttctg ttggaaaata 2101 tttggggttg aaataaacca gtgggagcat ggaaaaaaaa
     aaaaaaaaaa aaaaaaaaaa 2161 aaaaaa
```

In non-limiting examples, the method involves detecting and/or quantitating DENND1A Variant 2 mRNA by amplifying a segment of the mRNA, wherein the amplification products comprise SEQ ID NO:5, or a contiguous shorter segment thereof, wherein the continuous segment can exclude, for example, the poly-A tail. Thus, in one embodiment, the amplification product can comprise the distinct DENNDA1 Variant 2 (mRNA or cDNA) 3' open frame between and including nucleotide 1811-1913 and 3' UTR sequence from 1914-2132:

```
                                              (SEQ ID NO: 6)
1811            aaacaccatt gcaacaccag ctacactcca
     catcctacag aaaagcatta 1861 cccattttgc ggccaagttc ccgacgagag gctggacctc
     ttcatcacat tgacttacgc 1921 cgttgctttt ccagactggg cagaggggct gacttcgcag
     tgtgtgccaa agagccggtg 1981 tctgataatc ccattttcct gcttatcacc tgaactgtgt
     cagtatcact tttagttttg 2041 ttggttggtt ggtttgttgt ttgtttaata tgccctgttt
     tctacttctg ttggaaaata 2101 tttggggttg aaataaacca gtgggagcat gg
``` or a segment of SEQ ID NO:6 that is, for example, at least 10 nucleotides in length. The nucleotide numbering in this sequence is maintained from the full length cDNA sequence presented above. In one embodiment, the amplification products comprises a product that comprises at least 18 contiguous nucleotides of SEQ ID NO:6. In one embodiment, at least 18 contiguous polynucleotides are present in an amplification product that is from 24 to 200 base pairs (bp), inclusive and including all integers there between. In one embodiment, such an amplification product is from 80-100 bp. Those skilled in the art will recognize given the benefit of the present disclosure that a probe and/or primer for use in the invention can be complimentary or identical to a contiguous segment of SEQ ID NO:6. In one embodiment, such probe or primer is at least 18 nucleotides in length. In one embodiment, such probe or primer is from 18 to 24 nucleotides in length, inclusive, and including all digits there between. In certain embodiments, such probe or primer is identical or complementary to only the portion of DENND1A Variant 2 mRNA consisting of SEQ ID NO:6.

The invention accordingly provides primers which can amplify a polynucleotide comprising or consisting of SEQ ID NO:5 or SEQ ID NO:6.

In non-limiting embodiments, the primers that are used to detect and/or quantitate DENND1A Variant 2 mRNA are as follows: Forward Primer (5'-GGGCTGACTTCGCAGT-GTGT-3' SEQ ID NO:7), Reverse Primer (5-ACAGTTCA-GGTGATAAGCAGGAAA-3' SEQ ID NO:8).

In one embodiment, DENND1A Variant 2 mRNA can be measured via hybridization of a detectably labeled probe, and detecting the signal from the detectable label if the probe is hybridized to the mRNA, or its cDNA equivalent. The detectably labeled probe can be of the same length and nucleotide composition as described above for primers, or it can be longer. One non-limiting example of a probe that can be used in detecting/quantitating DENND1A Variant 2 mRNA has the sequence: CCAAAGAGC/ZEN/CGG TGT CTGATAATCCCA, (SEQ ID NO:9) wherein "ZEN" signifies location of a secondary quenching moiety which increases sensitivity of RT-PCR. The "ZEN" moiety is shown as in the probe at an illustrative location but can be positioned elsewhere in the probe, as desired. This probe can be used as an agent for detecting DENND1A Variant 2 mRNA or cDNA by hybridization to it, or it can be used, for instance, as a labeled probe that emits a detectable signal that is quenched during an assay such as RT-PCR.

The method of the invention includes in certain embodiments separating DENND1A Variant 2 mRNA from the biological sample, and mixing the separated DENND1A Variant 2 mRNA in a reaction container with non-naturally occurring reagents, including but not necessarily limited to synthetic oligonucleotide primers and/or probes. Additional reagents that can be added into the reaction mixture include but are not limited to salts, buffers and the like, a recombinant prokaryotic or bacteriophage DNA polymerase, free nucleoside triphosphates, etc.

In certain embodiments, testing a biological sample comprising or which could comprise DENND1A Variant 2 mRNA includes amplification of the DENND1A Variant 2 mRNA using a machine, such as a thermocycler, which subjects nucleic acids in the sample to successive rounds of heating (melting) and cooling to facilitate a PCR-based amplification of the mRNA into its cognate cDNA, or a segment thereof. Thus, in certain embodiments, the invention involves creating and/or testing a cDNA or a cDNA segment from DENND1A Variant 2 mRNA.

In certain embodiments, assaying of DENND1A Variant 2 is performed directly in cells or tissues, such as by immunohistochemical methods or in situ hybridizations.

In other embodiments, the DENND1A Variant 2 protein can be detected using any suitable technique or reagent, and will generally entail separating the DENND1A Variant 2 protein from the biological sample and reacting the separated protein with at least one specific DENND1A Variant 2 binding partner. Such binding partners can include but are not necessarily limited to antibodies, whether polyclonal or monoclonal, and antibody fragments that can specifically bind to the DENND1A Variant 2 protein, such as Fab fragments, Fab' fragments, F(ab')$_2$ fragments, Fd fragments, Fv fragments, and scFv fragments. Other DENND1A Variant 2 specific binding partners can include aptamers, diabodies, or any other reagent that can specifically recognize DENND1A Variant 2 protein. Detecting a complex of a specific binding partner and DENND1A Variant 2 protein can be performed using any suitable technique, including Western blotting, and other immunodetection methods, such as enzyme linked immunosorbant assay (ELISA), a lateral flow test, such as a urine or blood testing strip, and the like.

In certain embodiments, the invention includes use of binding partners that can distinguish the DENND1A Variant 2 protein from DENND1A Variant 1 protein by, for example, detecting these proteins after they have been separated from one another based on their size and/or mobility. In one illustrative embodiment, we used a monoclonal antibody (mAb) purchased from Aviva Systems Biology. The mAb is specific for the N-termini of DENND1A Variants 1 and Variant 2, and it accordingly can recognize each of these proteins, but can differentiate between them when they are separated based on their respective amino acid content. In particular, the DENND1A Variant 1 protein has an approximate size of 110 kD whereas the DENND1A Variant 2 protein has an approximate size of 62 kD. Thus, they can be distinguished from one another using a mAb in a variety of immune-detection methods, including but not necessarily limited to Western blotting.

In other embodiments, the invention can detect/quantitate DENND1A Variant 2 protein using a binding partner that is directed to one or more epitopes in its unique 33 amino acid C-terminus. The 33 amino acid sequence that is unique between DENND1A Variants 1 and 2 is: NTIATPATLHILQKSITHFAAKFPTRGW TSSSH (SEQ ID NO:10). We have employed polyclonal antibodies which are directed to a segment of this unique DENND1A Variant 2 C-terminal amino acid sequence. Specifically, we used DENND1A Variant 2 polyclonal antibody (rabbit) targeted to the following unique 15 amino acid sequence segment: QKSITHFAAKFP TRGWTSSSH (SEQ ID NO:11). We have utilized these polyclonal antibodies to detect DENND1A Variant 2 protein and have detected the same protein as obtained with the N-terminal antibody described above. The 15 amino acid sequence segment was chosen based on our analysis that predicted it to be optimally antigenic, and unlikely to result in production of antibodies that would have non-specific cross-reactivity with other proteins.

If desired, the determination of DENND1A Variant 2 mRNA and/or protein can be compared to a reference. The reference to which the Variant 2 mRNA and/or protein levels from the individual can be compared can be any suitable reference, examples of which include but are not limited to samples obtained from individuals who do not have the particular condition for which a diagnosis is sought, such as PCOS. Such references can include matched controls (i.e., matched for age, sex, or other demographics), a standardized curve(s), and/or experimentally designed controls such as known input RNA or protein used to normalize experimental data for qualitative or quantitative determination of the DENND1A Variant 2 from the sample for mass, molarity, concentration and the like. The reference level may also be depicted graphically as an area on a graph. In certain embodiments, determining Variant 2 mRNA and/or protein in a sample in an amount above a reference is a diagnosis of PCOS, or aids in a physician's diagnosis of PCOS. In certain embodiments, the reference is normal theca cells, which are compared to PCOS theca cells. In another embodiment, the reference is a sample that contains exosomes from an individual who does not have PCOS.

In certain embodiments, determining an increase in DENND1A Variant 2 mRNA of at least 1.5 fold in a sample as compared to a reference is a diagnosis of PCOS or aids in diagnosis of PCOS. In certain embodiments, the increase relative to a reference is at least 2.0, 3.0 or 4.0 fold, inclusive, and including all digits there between, and to the first decimal place.

In one aspect, the invention includes determining whether or not a subject is a candidate for receiving a prophylactic or therapeutic treatment for a condition that is positively correlated with DENND1A Variant 2 expression. In one embodiment the condition is PCOS. The method generally comprises testing a sample from the subject for the presence or absence or amount of DENND1A Variant 2. The presence of DENND1A Variant 2 or of an amount of DENND1A Variant 2 above a reference is indicative that the individual is a candidate for a prophylactic or therapeutic intervention for PCOS. In one embodiment, the method further comprises treating the individual for PCOS. The individual can be treated with any PCOS intervention, including but not limited to surgical interventions. Additional non-limiting examples of therapies include ovulation induction with clomiphene citrate or gonadotropins for women seeking to establish a pregnancy or oral contraceptive pills for women seeking symptomatic relief for manifestations of hyperandrogenemia. Weight loss or drugs like metformin can be used to treat metabolic features of PCOS.

In another aspect, the invention includes monitoring treatment of patient for a condition that is positively correlated with DENND1A Variant 2 expression. In one embodiment the condition is PCOS. The method comprises optionally testing a sample from the individual to establish the presence and/or amount or other value for DENND1A Variant 2 expression at the mRNA and/or protein level, and accordingly provides an initial DENND1A Variant 2 expression value. During or subsequent to treatment, the method comprises obtaining and testing a sample from the individual to establish the presence and/or amount or other value for DENND1A Variant 2 expression at the mRNA and/or protein level, and accordingly provides a treatment value. The treatment value can be determined over multiple time points. A reduction in the treatment value (i.e., a reduction in DENND1A Variant 2 mRNA or protein) relative to the initial value, and/or a reduction over the course of treatment is considered to be indicative that the treatment is effective. A lack of change for the treatment value relative to an initial value or to treatment values over time is indicative that the treatment is not effective, and/or that an alternative treatment should be considered.

In one embodiment, the invention provides a closed or sealed package or container that contains compositions useful for testing biological samples for DENND1A Variant 2 mRNA or protein. The compositions can include primers or probes as have been further described herein, and can include reagents used for hybridization of the probes or primers for nucleic acid amplification or for direct nucleic acid detection, for protein extraction and testing, and can include reagents for processing of a biological sample, such as for processing of liquid biological samples that could contain DENND1A Variant 2 mRNA or protein. In certain embodiments, the package can comprise one or more closed or sealed vials, bottles, or any other suitable containers or packaging comprising reagents, and which are designed for the sale, or distribution, containment, or use of the reagents. In addition to the reagents for detecting DENND1A Variant 2 mRNA or protein, the package can contain printed information. The printed information can be provided on a label, or on a paper insert, or printed on the packaging material itself. The printed information can include information that identifies the contents of the package, an indication of what marker the reagents are intended to detect and/or what condition the marker is related to, such as PCOS, and instructions for using the contents of the package for testing. In certain embodiments, the packages are considered to be kits.

In various embodiments, the invention comprises fixing in a tangible medium the result obtained by testing for DENND1A Variant 2 mRNA or protein. The tangible medium can be any type of tangible medium, such as any type of digital medium, including but not limited to a DVD, a CD-ROM, a portable flash memory device, or a printed or digitized report, etc., such as a spreadsheet or word processing document. The invention includes providing the tangible medium to a health care provider to assist with development of a diagnosis and/or recommendation for treatment of the individual and/or for developing a prognosis for the individual, such as for treating PCOS.

The following description and specific Examples are provided to illustrate the invention, but are not intended to be limiting in any way. Example 10 provides an expanded description of materials and methods used to obtain the data as further described below by way of Examples 1 through 9.

EXAMPLE 1

This Example provides data obtained from analysis of CYP17 mRNA accumulation and DHEA biosynthesis. FIGS. 1A and 1B provide graphical summaries of data which demonstrate that both basal and cAMP-stimulated CYP17 mRNA accumulation and DHEA production are increased in PCOS theca cells propagated in long-term culture. FIG. 1A shows that CYP17 mRNA abundance was evaluated in fourth passage theca cells that were isolated from 5 independent normal cycling women and 5 independent women with PCOS that were grown to subconfluence and transferred into serum free medium with vehicle, (Control conditions) or 20 µM forskolin (F). 16 h following treatment, mRNA was harvested, and CYP17 mRNA accumulation was measured using quantitative real-time PCR analysis. CYP17 mRNA values are normalized by TBP mRNA and are presented as relative abundance. As demonstrated by the data depicted in FIG. 1A, CYP17 mRNA accumulation was significantly increased in PCOS theca cells as compared to normal theca cells treated under basal and forskolin stimulated conditions (*, P<0.05). To evaluate whether androgen biosynthesis is increased in theca cells isolated from PCOS women as compared to normal cycling women, fourth passage theca cells isolated from multiple normal and PCOS women were treated in the presence or absence (Control) of 20 µM forskolin (F). Following 72 h of treatment, the media was collected, DHEA production was evaluated by ELISA, and the data were normalized to cell number. Results are presented as the mean±SEM of steroid levels from triplicate theca cell cultures from 4 independent normal and PCOS women. As shown in FIG. 1B, DHEA biosynthesis in PCOS theca cells was significantly increased under both basal and forskolin stimulated conditions (*, P<0.05).

EXAMPLE 2

Figure 2:
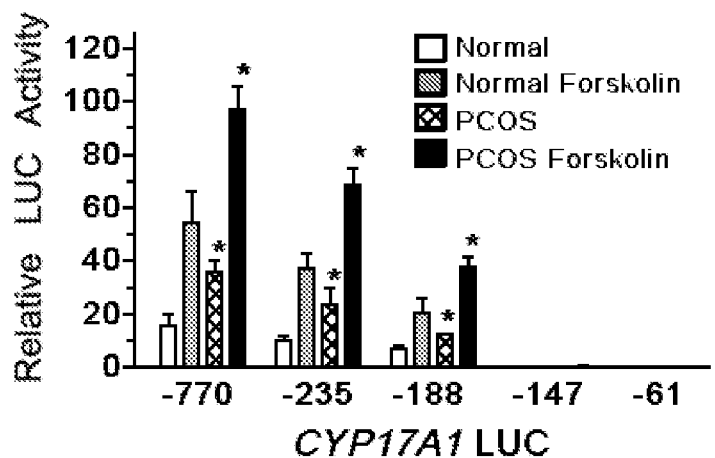
FIG. 2 provides a graphical representation of data obtained from deletion analysis of the CYP17A1 promoter in normal and PCOS theca cells and demonstrates that CYP17A1 promoter activity is increased in PCOS theca cells, under basal and forskolin-stimulated conditions (*, P<0.01), as compared to normal theca cells for individual promoter constructs.

This Example provides a description of data obtained from analysis of CYP17A1 promoter activity. To compare the transcriptional regulation of the CYP17A1 gene in normal and PCOS theca cells, cells were transiently transfected with pGL3 luciferase constructs containing −770, −235, −188, −147, or −61 to +44 bp of the 5′-flanking sequence of the CYP17A1 gene. All constructs contain the endogenous TATA box and transcriptional start site. Fourth passage theca cells from normal cycling and PCOS women were transiently transfected with the above constructs. Following transfection, cells were cultured in transfection medium alone or with forskolin (20 µM) for 24 h. Data are presented as relative luciferase (LUC) activity that was normalized with β-galactosidase activity, and represent the mean±SEM of independent experiments in 5 normal and 5 PCOS theca cell cultures. As shown in FIG. 2, CYP17A1 promoter activity was significantly increased in PCOS theca cells, under basal and forskolin-stimulated conditions (*, P<0.01), as compared to normal theca cells for individual promoter constructs.

EXAMPLE 3

Figure 3:
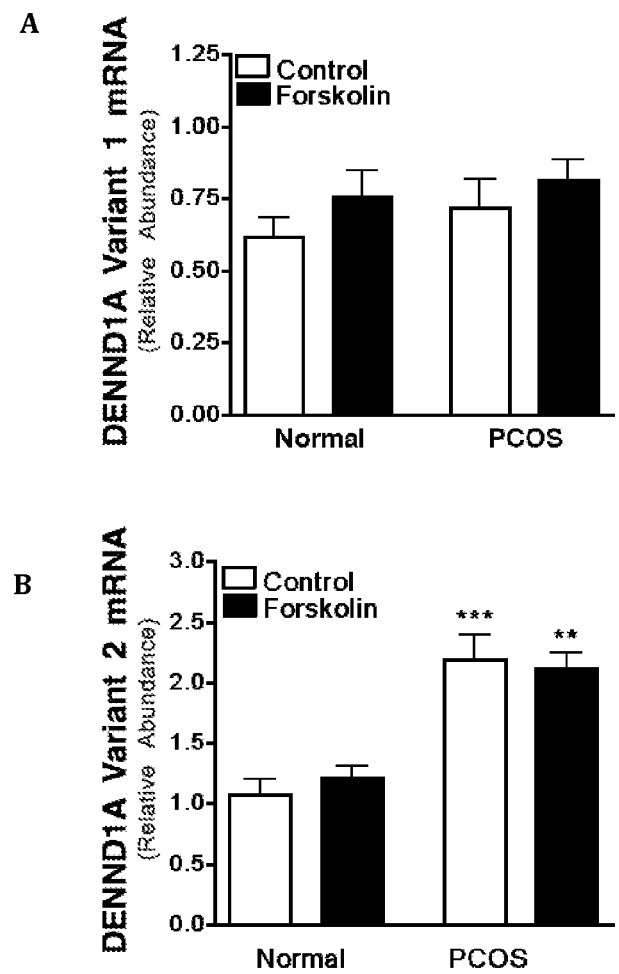
FIGS. 3A and 3B provide graphical representations of data demonstrating that DENND1A Variant 2 mRNA accumulation is greater in PCOS theca cells compared to normal theca cells.
Figure 4:
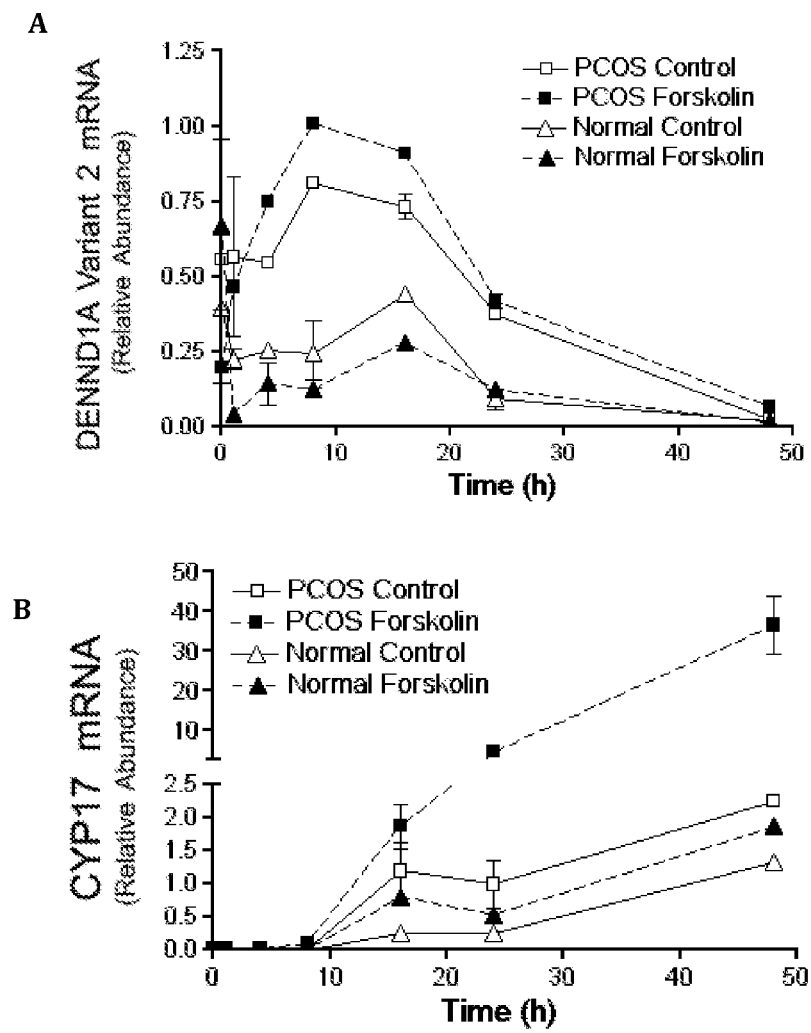
FIGS. 4A and 4B provide graphical representations of data demonstrating that DENND1A Variant 2 mRNA accumulation precedes CYP17 mRNA accumulation in normal and PCOS theca cells. The time courses of DENND1A Variant 2 (FIG. 4A) and CYP17 (FIG. 4B) mRNA accumulation was examined in normal and PCOS theca cells treated in serum free medium for 0, 4, 8, 16, 24, or 48 h in the presence and absence of 20 µM forskolin. Specifically, as shown in FIG. 4A, DENND1A.V2 mRNA accumulation increases rapidly between 4-8 h and plateaus around 16-20 h in PCOS cells (FIG. 4A). In contrast, CYP17 mRNA accumulation increases in response to forskolin treatment over 8-48 h, with ~2-3 fold increase in forskolin stimulated CYP17 mRNA in normal cells, and ~10-40 fold increase in PCOS cells (FIG. 4B).

This Example provides data and a description of analysis of DENND1A mRNA accumulation in normal and PCOS cells and time course. The data from this analysis are summarized in FIGS. 3 and 4.

FIG. 3A shows that DENND1A Variant 1 mRNA is not differentially expressed in normal and PCOS theca cells. DENND1A Variant 1 and Variant 2 mRNA accumulation was quantitated in fourth passage theca cells isolated from 5 individual normal and 5 individual PCOS women that were grown in culture until subconfluence, then treated with and without 20 µM forskolin, an activator of adenylate cyclase for 16 h in serum free medium. Following treatment RNA was harvested and DENND1A Variant 1 (FIG. 3A) and Variant 2 (FIG. 3B) mRNA abundance was quantitated by Real-Time PCR analysis, and normalized using TBP mRNA abundance. The comparison of DENND1A Variant 1 mRNA accumulation normal and PCOS theca cells demonstrated no statistical difference in basal and forskolin-stimulated DENND1A Variant 1 mRNA accumulation in normal and PCOS theca cells (FIG. 3A). In contrast, DENND1A Variant 2 mRNA accumulation was significantly increased under both basal (*, P<0.01) and forskolin (, P<0.05) stimulated conditions in PCOS theca cells, as compared to normal cells (FIG. 3B).

FIGS. 4A and 4B show that DENND1A Variant 2 mRNA accumulation precedes CYP17 mRNA accumulation in normal and PCOS theca cells. The time courses of DENND1A Variant 2 (FIG. 4A) and CYP17 (FIG. 4B) mRNA accumulation was examined in normal or PCOS theca cells treated in serum free medium for 0, 4, 8, 16, 24, or 48 h in the presence and absence of 20 μM forskolin. DENND1A Variant 2 and CYP17 mRNA abundance was measured using quantitative Real-Time PCR and normalized by TBP abundance. DENND1A.V2 mRNA accumulation increases rapidly between 4-8 h and plateaus around 16-20 h in PCOS cells (FIG. 4A). In normal cells, the same trend is observed, although it is less rapid and lower in magnitude. In agreement with the data in FIG. 3B, DENND1A.V2 mRNA accumulation is elevated ~2-3 fold in PCOS cells as compared to normal cells. In contrast, CYP17 mRNA accumulation increases in response to forskolin treatment over 8-48 h, with ~2-3 fold increase in forskolin stimulated CYP17 mRNA in normal cells, and ~10-40 fold increase in PCOS cells (FIG. 4B). The data presented in each of FIGS. 4A and 4B were obtained from 2 normal and 2 PCOS patients, that are representative of data collected from theca cells from 5 normal and 5 PCOS patients.

EXAMPLE 4

Figure 5:
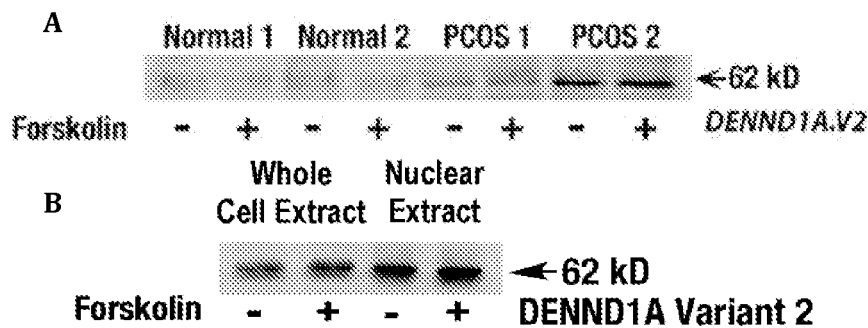
FIGS. 5A and 5B provide a photographic representation of Western Blot analysis demonstrating that DENND1A Variant 2 protein expression is increased in PCOS theca cells.

This Example presents a characterization of the proteins encoded by DENND1A Variants 1 and 2 via Western Blot analysis. To evaluate DENND1A protein in human theca cells Western Blot analysis was performed in whole cell and nuclear extracts. To compare DENND1A protein expression in normal and PCOS theca cells, Western blot analysis was performed with 35 μg of whole cell extracts from theca cells isolated from multiple normal and PCOS patients treated with and without 20 μM forskolin for 24 h. From the results of these experiments we expected bands at approximately 110 kD, corresponding to DENND1A Variant 1, and at approximately 62 kD corresponding to DENND1A Variant 2. As shown in FIG. 5A, representative Western Blot analysis demonstrates increased 62 kD DENND1A Variant 2 (DENND1A.V2) in PCOS theca cells. In FIG. 5B, comparison of 25 μg of whole cell extracts and nuclear extracts from PCOS theca cells treated with and without 20 μM forskolin for 24 h, showed that 62 kD DENND1A Variant 2 was present in the nuclear component of PCOS theca cells. 110 kD DENND1A Variant 1 was not detected in normal or PCOS whole cell or nuclear extracts.

EXAMPLE 5

This Example describes the effects of DENND1A Variant 2 expression on DHEA and CYP17 mRNA accumulation.

To examine the effects of DENND1A Variant 2 on DHEA biosynthesis and CYP17 mRNA accumulation we obtained a DENND1A.V2 expressing adenovirus from Applied Biological Materials, Richmond, BC.

DENND1A.V2 adenovirus (i.e., hDENND1A.V2-pADenoG) was constructed by cloning DENND1A.V2 from pCMV6-XL4 plasmid encoding the DENND1A Variant 2 into pADenoG, from Origene, Rockville, Md. A control or Null adenovirus (Null-pAdenoG adendovirus, was also obtained from Applied Biological Materials. Richmond, BC.

Figure 6:
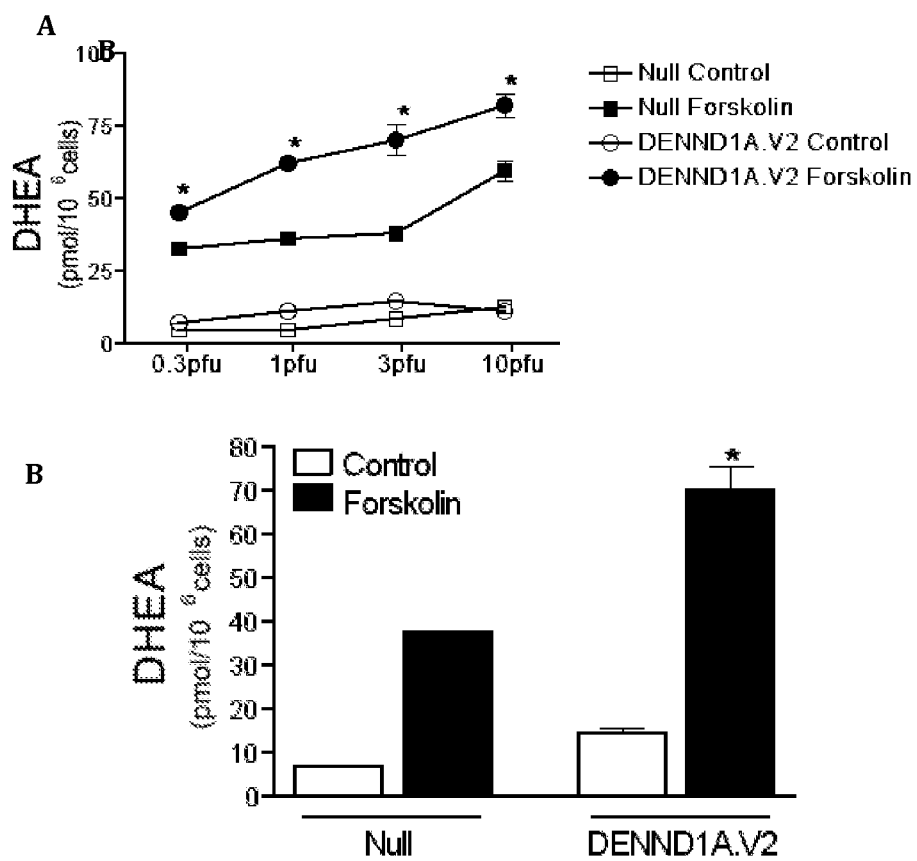
FIGS. 6A, 6B, 6C and 6D provide graphical representations of data demonstrating that expression of DENND1A Variant 2 in normal theca cells results in elevated androgen production, augmented CYP17 mRNA accumulation, and increased CYP17A1 promoter regulation.
Figure 6:
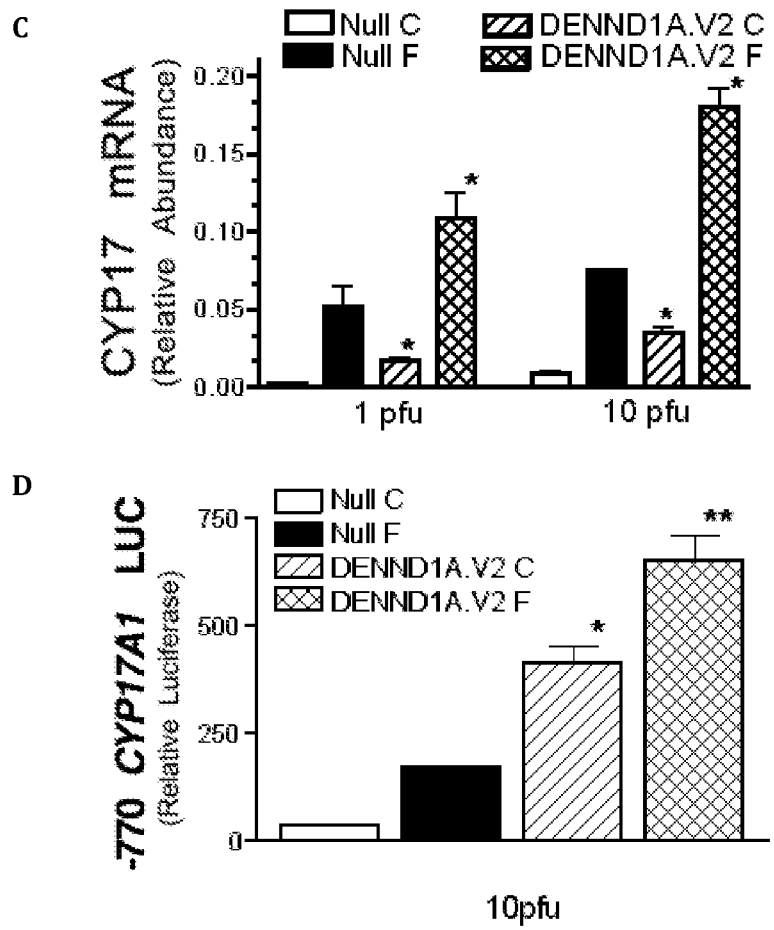

In these experiments 6-well plates of fourth passage normal theca cells were infected with 0.3, 1.0, 3.0, and 10 pfu/cell of either empty (Null) or DENND1A.V2 expressing adenovirus, treated with or without 20 μM forskolin in serum free medium. Following 72 h treatment DHEA in the media was quantitated. As shown in FIG. 6A, infection with all doses of DENND1A.V2 adenovirus significantly increased forskolin-stimulated DHEA production (*, P<0.05) compared with control Null adenovirus (FIG. 6A). Subsequent infection of normal theca cells with 3.0 pfu of adenovirus expressing DENND1A.V2 showed a significant increase in forskolin stimulated DHEA biosynthesis (*, P<0.05) compared to Null infected cells (FIG. 6B). To examine the effects of DENND1A.V2 expression on CYP17 mRNA accumulation, 100 mm cultures of fourth passage normal theca cells were infected with 1.0 pfu/cell DENND1A.V2 adenovirus, or Null adenovirus, and treated with or without 20 μM forskolin for 16 h. Following treatment, RNA was harvested, and CYP17 mRNA abundance was quantitated using a single step Brilliant III Ultra Fast QRT-PCR protocol and normalized by TBP abundance. As shown in FIG. 6C, 10 pfu DENND1A.V2 adenovirus significantly increases CYP17 mRNA accumulation in normal cells, with and without forskolin stimulation (*, P<0.05), as compared to infection with Null adenovirus.

EXAMPLE 6

This Example provides a description of the effects of DENND1A Variant 2 expression on CYP17A1 promoter regulation.

To examine the effects of DENND1A Variant 2 on CYP17A1 gene transcription, theca cells were transfected with CYP17A1 reporter gene constructs containing −770/+44 of the 5'-flanking regions of the human CYP17A1 gene fused to the luciferase. This construct was constructed by subcloning the 770/+44 (KpnI/NaeI) fragment of the CYP17A1 5' flanking sequence into the luciferase pGL3 basic vector (Promega Corp, Madison, Wis.).

In these experiments fourth passage normal theca cells on 6-well plates were transfected using calcium phosphate in a 3% $CO_2$, 95% ambient air, 37 C incubator. The transfection reaction contained 2 μg/well of promoter luciferase plasmid, and 100 ng/well of plasmid, expressing β-galactosidase (used for normalization of transfection efficiency between replicates and transfection experiments). One hour following the transfection the cells were glycerol shocked in 15% glycerol and infected with the DENND1A.V2 (hDENND1A.V2-pADenoG) or Null-pAdenoG adenovirus. hDENND1A.V2-pADenoG which were custom ordered from Applied Biological Materials, BC. One hour thereafter the cells were treated with serum-free medium with and without 20 μM forskolin, an activator of adenylate cyclase. 24 h thereafter the media was removed and the cells were frozen, resuspended in reporter lysis buffer (Promega, Madison, Wis.), and luciferase activity was determined utilizing the Luciferase Assay System (Promega, Madison, Wis.) on a Sirius Luminometer (Zylux Corp., TN). β-Gal activity was determined using a Galacto-Light Plus System (Applied Biosystems, Grand Island, N.Y.). Transfections were performed in triplicate, normalized using β-galactosidase, and calculated±SEM. The results of the experiments shown in FIG. 6D demonstrate that expression of DENND1A Variant 2 significantly stimulated both basal (*, P<0.05) and forskolin-stimulated (*, P<0.01) CYP17A1 promoter function in theca cells, compared to control plasmid. We believe these are the first data to suggest that DENND1A Variant 2 has the capacity to augment CYP17A1 gene expression in human theca cells.

EXAMPLE 7

Figure 7:
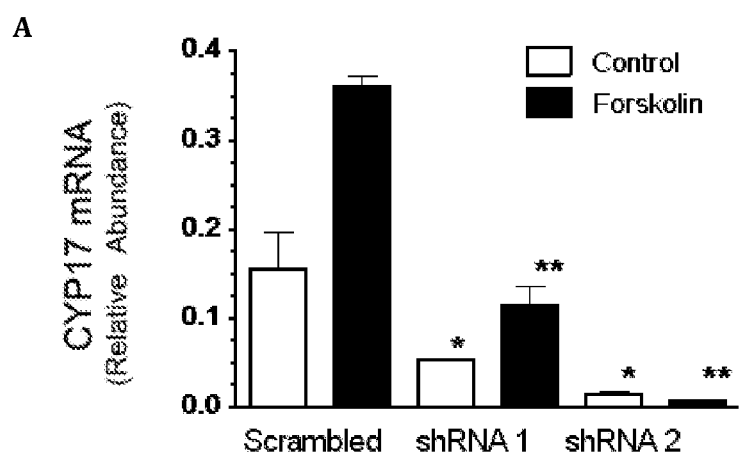
FIGS. 7A, 7B and 7C provide graphical representations of data demonstrating that knockdown of DENND1A Variant 2 in PCOS theca cells results in decreased CYP17A1 promoter regulation, CYP17 mRNA levels, and androgen biosynthesis.
Figure 7:
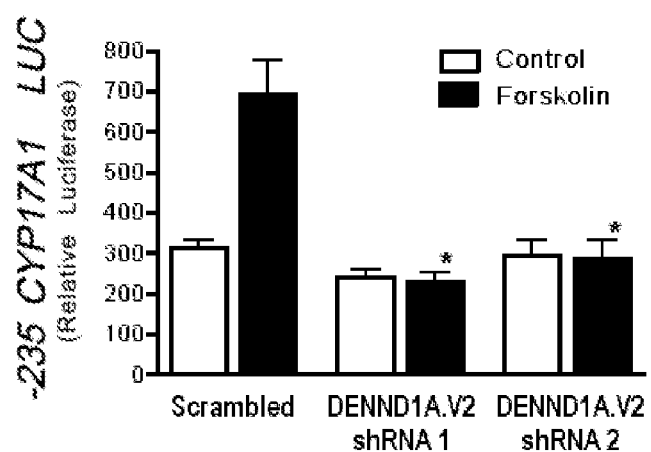
Figure 7:
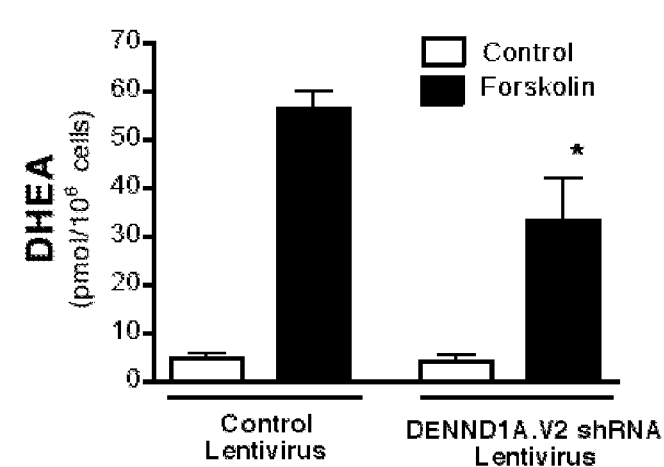

This Example provides a description of the effects of DENND1A Variant 2 shRNA1 and shRNA2 retrovirus plasmids on CYP17 mRNA and CYP17A1 promoter regulation, as well as the effects of DENND1A Variant 2 shRNA lentivirus particles on DHEA biosynthesis. To investigate whether a reduction of DENND1A.V2 expression reduces elevated CYP17 mRNA in PCOS theca cells, silencing DENND1A.V2 shRNA retrovirus plasmids were transfected into PCOS theca cells and CYP17 message was assessed. PCOS theca cells were transfected with DENND1A.V2 shRNA retroviral plasmids and control plasmids from Origene, in pRSV (HUSH) retrovirus plasmids. The DENND1A retroviral shRNA1 plasmid was targeted to DENND1A.V2 sequence 5'-CGACGAGAGGCTGGAC-CTCTTAC-3.' (SEQ ID NO:12). The DENND1A.V2 shRNA2 retrovirus plasmid was targeted to 5'-CCTCT-TCATCACATTGACTTACG-3' (SEQ ID NO:13). Briefly, in these experiments fourth passage theca cells were transfected on 100 mm dishes with Genejuice transfection reagent (Novagen, Madison, Wis.) and 4 µg/dish empty expression vector or 4 µg/dish pRSV-Scrambled or plasmids specific to DENND1A Variant 2, i.e., pSV-shRNA1 or pRSV-shRNA2 in Optimen medium in a 3% CO2, 95% ambient air, 37 C incubator. Following 6 h transfection the cells were rinsed with PBS, and treated in serum-free medium with and without 20 µM forskolin an activator of adenylate cyclase. 24 h thereafter the media was removed and the cells were frozen, total RNA harvested, and CYP17 and TBP mRNA abundance was quantitated using a single step Brilliant III Ultra Fast QRT-PCR protocol. As shown in FIG. 7A, DENND1A.V2 shRNA1 and shRNA2 significantly inhibited both basal (*, P<0.05) and forskolin stimulated CYP17 mRNA accumulation (*, P<0.01) in PCOS theca cells.

Studies were performed to evaluate whether silencing shRNAs specific to DENND1A.V2 could reduce CYP17A1 promoter activity. To examine the effects of knockdown of DENND1A Variant 2 mRNA on CYP17A1 transcription, PCOS theca cells were transfected with CYP17A1 reporter gene constructs containing −235/+44 of the 5'-flanking regions of the human CYP17A1 gene fused to the luciferase. This construct was made by subcloning the −235/+44 (SacI/NaeI) fragment of the 5' flanking sequence of the CYP17A1 promoter into the luciferase pGL3 basic vector using pGL3 (Promega Corp., Madison, Wis.). In these experiments fourth passage theca cells were transfected with Genejuice transfection reagent (Novagen, Madison, Wis.) in Optimem medium in 12-well plates in a 3% CO2, 95% ambient air, 37 C incubator. The transfection reaction contained 250 ng/well of promoter luciferase plasmid, and 2.5 ng/well of pRL plasmid, expressing renilla (used for normalization of transfection efficiency between replicates and transfection experiments). Scrambled pRV expression vector or plasmid encoding the DENND1A Variant 2 pRV-shRNA1 or pRV-shRNA2, from Origene, Rockville, Md. was also added to the transfection reaction at 1 µg/well. Following 6 h transfection the cells were rinsed with PBS, and treated in serum-free medium with and without 20 µM forskolin as an activator of adenylate cyclase. 24 h thereafter the media was removed and the cells were frozen, resuspended in reporter lysis buffer (Promega, Madison, Wis.), and luciferase activity was determined utilizing the Dual Luciferase Assay System (Promega, Madison, Wis.) on a Sirius Luminometer (Zylux Corp., TN). Transfections were performed in triplicate, normalized using renilla, and calculated±SEM.

These experiments showed that co-transfection of PCOS theca cells with DENND1A.V2 shRNA1 or shRNA2 retrovirus plasmid resulted in a significant inhibition of forskolin-stimulated CYP17A1 reporter activity (*, P<0.05), compared to Scrambled shRNA (FIG. 7B). The results from these experiments show that transfection of DENND1A Variant 2 shRNA1 and shRNA2 inhibit both basal and cAMP-dependent CYP17A1 reporter activity in PCOS theca cells, compared to scrambled shRNA. These data demonstrate that DENND1A Variant 2 confers increased transcriptional activation of CYP17A1 gene expression in PCOS theca cells.

To evaluate the effect of knockdown of DENND1A.V2 on DHEA biosynthesis, PCOS theca cells were infected with a silencing shRNA DENND1A.V2 lentivirus or a control non-silencing lentivirus in the presence or absence of forskolin for 72 h as detailed above and with the following modifications. We utilized custom Thermo/Dharmacon GIPZ DENND1A.V2 shRNA particles. This shRNA lentivirus targets the mRNA equivalent of the DENND1A.V2 sequence 5'-CTCTTCATCACATTGACTT-3' (SEQ ID NO:14). 100 mm tissue culture dishes of 50% confluent PCOS theca cells were infected with 300,000 particles of silencing shRNA DENND1A.V2 lentivirus or a control non-silencing lentivirus in serum free medium with 5 µg/mL polybrene in serum free medium. Six hours thereafter the lentivirus mixture was removed the cells were transferred into serum free medium in the presence or absence of forskolin for 72 h. As shown in FIG. 7C, infection with silencing shRNA DENND1A.V2 lentivirus significantly inhibited forskolin stimulated DHEA biosynthesis (*, P<0.05). Combined these data support that knockdown of DENND1A Variant 2 mRNA expression using shRNA/siRNA methodology results in inhibition of augmented CYP17A1 gene expression, CYP17 mRNA and androgen biosynthesis in PCOS theca cells.

EXAMPLE 8

Figure 8:
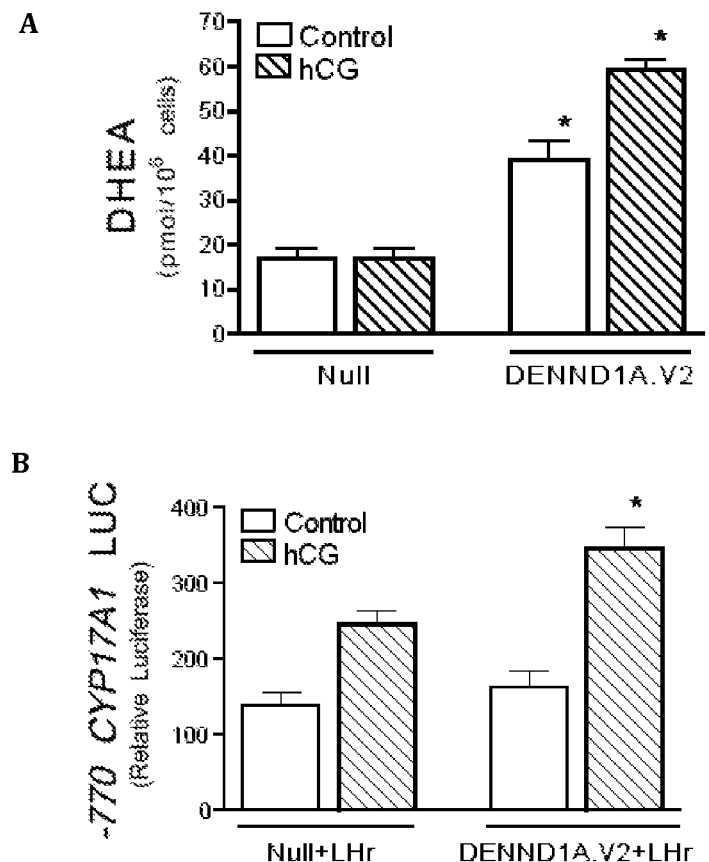
FIGS. 8A and 8B provide graphical representations of data demonstrating that DENND1A.V2 enhances LH/hCG-dependent changes in DHEA and CYP17A1 promoter regulation.

The Example demonstrates the effects of DENND1A Variant 2 on LH/hCG dependent changes on DHEA and CYP17A1 promoter activity. The data are summarized in FIGS. 8A and 8B. Briefly, to examine whether DENND1A.V2 affects LH/hCG-dependent DHEA biosynthesis, normal theca cells were infected with 3 pfu/cell Null or DENND1A.V2 adenovirus, and treated with and without 1.0 IU/mL hCG for 72 h. As shown in FIG. 8A, hCG had no significant effect on DHEA biosynthesis in Null treated cells. In contrast, DENND1A.V2 significantly increased DHEA biosynthesis (*, P<0.05) over control Null infected cells. DENND1A.V2 infection also significantly enhanced hCG-stimulated (*, P<0.05) DHEA biosynthesis (FIG. 8A). To examine whether DENND1A.V2 affects LH/hCG-dependent CYP17A1 expression, normal theca cells were transfected with the −770 CYP17A1 luciferase construct, then infected with 3 pfu/cell Null or DENND1A.V2 adenovirus. LHCGR expressing adenovirus (1.0 pfu/cell) was included in the infection to ensure that LH receptor was not limiting. Following transfection/infection, the cells were treated with and without 1.0 IU/mL hCG for 48 h. As shown in FIG. 8B, hCG-stimulated CYP17A1 promoter function is increased in DENND1A.V2 infected cells.

EXAMPLE 9

Figure 9:
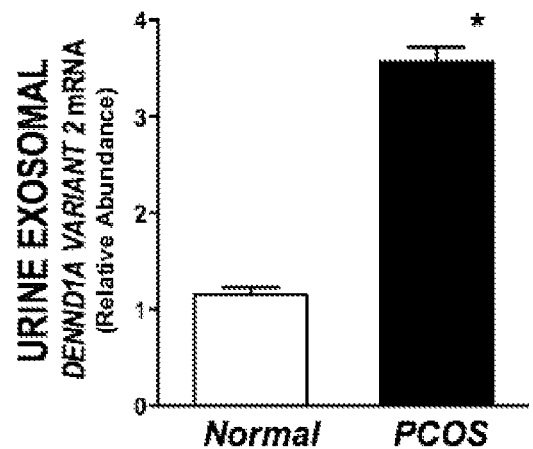
FIG. 9 provides a graphical representation of data demonstrating that DENND1A Variant 2 mRNA is increased in urine exosomes isolated from PCOS women as compared to urine exosomes from normal women. In particular, DENND1A Variant 2 mRNA is significantly increased in urine exosomes isolated from PCOS women (*, P<0.01), as compared to normal cycling women.

The Example demonstrates that the invention is suitable for detecting DENND1A Variant 2 in urine. In order to establish this, DENND1A Variant 2 mRNA abundance was compared in exosomal RNA isolated from urine from normal cycling and PCOS women. Mid-day urine samples were obtained from both populations of women, and were serially centrifuged at 300 g at 4 C for 10 minutes, 2000 g 4 C for 10 minutes, and 12,000 g at 4 C for 30 minutes. Exosomal RNA was then extracted from the supernatant using a modified protocol for, Urine exosome RNA Isolation, from Norgen, (Thorold, CAN). DENND1A Variant 2 mRNA abundance was then quantitated using Real-Time PCR and normalized using 5S mRNA abundance. As shown in FIG. 9, DENND1A Variant 2 mRNA is significantly increased in urine exosomes isolated from PCOS women (*, $P<0.01$), as compared to normal cycling women. Thus, we have determined that the DENND1A Variant 2 can be detected in urine, and if desired can be compared to a reference to establish a positive correlation of the DENND1A Variant 2 in urine with PCOS.

EXAMPLE 10

This Example provides a description of materials and methods used to conduct experiments described in the foregoing Examples.

Theca cell isolation and propagation. With respect to theca cell isolation and propagation for use in the Examples described below, for all of the experiments in which we obtained data from highly characterized normal and PCOS theca cells, isolated human ovarian tissue from individual follicles of normal cycling and PCOS women that have been isolated, banked, grown and passaged in long-term culture was used. Human theca interna tissue was obtained from follicles of women undergoing hysterectomy, following informed consent under an IRB protocol approved by the Institutional Review Board of the Pennsylvania State University College of Medicine. Individual follicles were dissected away from ovarian stroma, and dispersed with 0.05% collagenase I, 0.05% collagenase IA, and 0.01% deoxyribonuclease, in medium containing 10% fetal bovine serum (FBS), with antibiotics. The isolated follicles were size-selected for diameters ranging from 3-5 mm so that theca cells derived from follicles of similar size from normal and PCOS subjects could be compared. Theca cells were cultured on fibronectin coated dishes utilizing previously described growth medium (1:1 mixture of Dulbecco's Eagles Medium (DME) and Hams F-12 medium containing 5% FBS, 5% horse serum (HS), 2% UltroSer G, 20 nM insulin, 20 nM selenium, 1 μM vitamin E, and antibiotics). Sera and growth factors were obtained from the following sources: FBS and DME/F12 (Irvine Scientific, Irvine, Calif.): horse serum (Life Technologies, Grand Island, N.Y.); UltroSer G (Reactifs IBF, Villeneuve-la-Garenne, France): other compounds were purchased from Sigma (St. Louis, Mo.). The cells were grown in reduced oxygen tension (5% O2, 90% N2, and 5% CO2) and given supplemental antioxidants (vitamin E and selenium) to prevent oxidative damage.

Experiments comparing PCOS and normal theca were performed utilizing fourth passage (31-38 population doublings) theca cells isolated from size-matched follicles obtained from age-matched subjects. The use of fourth passage cells allowed us to perform multiple experiments from the same patient population, and were propagated from frozen stocks of second passage cells in the media described above. For all studies, theca cell cultures obtained from numerous independent patients were examined, for confirmation. The passage conditions and split ratios for all normal and PCOS cells were identical.

The PCOS and normal ovarian tissue came from age-matched women, 38-40 years old. The diagnosis of PCOS was made according to NIH consensus guidelines, which include hyperandrogenemia, oligoovulation, polycystic ovaries, and the exclusion of 21α-hydroxylase deficiency, Cushing's syndrome, and hyperprolactinemia. All of the PCOS theca cell preparations studied came from ovaries of women with fewer than six menses per year and elevated serum total testosterone or bioavailable testosterone levels. Each of the PCOS ovaries contained multiple subcortical follicles of less than 10 mm in diameter. The control (normal) theca cell preparations came from ovaries of fertile women with normal menstrual histories, menstrual cycles of 21-35 days, and no clinical signs of hyperandrogenism. Neither PCOS nor normal subjects were receiving hormonal medications at the time of surgery. Indications for surgery were dysfunctional uterine bleeding, endometrial cancer, and/or pelvic pain.

Quantitating DENND1A Variant 1, DENND1A Variant 2, and CYP17 mRNA. For those data presented below wherein mRNA is quantitated, the following materials and methods were used.

DENND1A Variant 1, DENND1A Variant 2, CYP17, TATA Box Binding Protein (TBP), and 5S Ribosomal RNA abundance were determined by quantitative Real-Time PCR utilizing the single step Brilliant III Ultra Fast QRT-PCR Master Mix (Agilent) using 100 μg total RNA/tube, final concentration of each forward and reverse primers we determined using the manufacturers specifications. The specific primer and probe sequences used are provided below in detail.

The DENND1A Variant 2 specific mRNA Primer and Probe set used was specific to the DENND1A 3'UTR sequence, the entire sequence of which is presented here beginning at nt 1914 (except for the polyA tail):

```
                                              (SEQ ID NO: 15)
1914
            cttacgc 1921   cgttgctttt  ccagactggg  cagaggggct  gacttcgcag
       tgtgtgccaa  agagccggtg 1981   tctgataatc  ccattttcct  gcttatcacc  tgaactgtgt
       cagtatcact  tttagttttg 2041   ttggttggtt  ggtttgttgt  ttgtttaata  tgccctgttt
       tctacttctg  tggaaaata 2101   tttggggttg  aaataaacca  gtgggagcat  gg
```

To amplify the unique DENND1A 3'UTR described above, the following primers were used: Forward Primer (5'-GGGCTGACTTCGCAGTGTGT-3'- (SEQ ID NO:7); Reverse Primer (5-ACAGTTCAGGTGATAAGCAG-GAAA-3'- SEQ ID NO:8); Probe (5'/56-FAM/CCAAAGAGC/ZEN/CGG TGT CTGATAATCCCA/3IAB-KFQ/-3'- (SEQ ID NO:9)). (Position NM_024820.2, Forward 1951, Probe 1967, Reverse start 5'-2018). 200 nM primers and 200 nM probe used for the reaction. We selected these particular primer and probes sequences to mitigate the likelihood they would anneal to other mRNAs that could be present in the samples.

The DENND1A Variant 1 specific mRNA Primer and Probe set Forward Primer (5'-GGATTCATTTCCATAAAC-CAAGTTAAA-3' SEQ ID NO:16) Reverse Primer (5'-CACAATTTCCTGCGTGTCTCA3' SEQ ID NO:17), Probe (5'/56-FAM/ATGGCCCGA/ZEN/CCATTT AAGAAAACAACCA/#IA3BkFQ/-3 SEQ ID NO:18) (Position NM_024820.1, Forward 4434, Probe 4463, Reverse start5'4513). 200 nM primers and 200 nM probe used for the reaction.

The CYP17 mRNA Primer and Probe set. Forward primer (5'-GGCCTCAAA TGGCAAC TCTAGA-3' SEQ ID NO:19): Reverse Primer (5'-CTTCTGATCGCCATCCTT-GAA-3' SEQ ID NO:20): Probe (5' 6-FAM-TCGCGTC-CAACAACCGTAAGGGTATC-3' BHQ-1.3' SEQ ID NO:21). (Position NM_00012, Forward 328, Probe 391, Reverse start 5' 464). 200 nM primer and probe.

TATA-box binding protein (TBP) mRNA Primer and Probe set. TBP was determined for each cDNA sample in theca cells for normalization. Forward Primer (5'-CACGGC ACTGATTTTCAGTTC-3' SEQ ID NO:22). Reverse Primer (5'-TCTTGCTGCCAGTCTGGACT-3' SEQ ID NO:23), Probe (5'-JOE-TGTGCACAGGAGCCAAGAGTGAAGA-3' BHQ-1,3 SEQ ID NO:24').

5S Ribosomal RNA Primer and Probe set. 5S was determined for each cDNA sample in urine exosomal RNA for normalization. Forward Primer (5'-GCCTCCTTCA-GCGTCTAC), Reverse Primer (5'GTCTCCCATCCAAG-TACTAACC-3' SEQ ID NO:25 Probe (5"HEX-TCTCGTCTG/ZEN/ATCTCGGAAGCTAAGCA-3'IABKFQ-1' SEQ ID NO:26). (Position X51545, Forward 262, Probe 306, Reverse start 5' 343). 50 nM primers and 50 nM probe used for the reaction.

The gene specific one step PCR was carried out in duplicate for each mRNA sample and for a series of serial dilutions in an Mx3000 Thermocycler system (Stratagene, Santa Clara, Calif.) according to manufacturers instructions for this instrument. An arbitrary value of RNA template was assigned to each serial dilution (ie, 1000, 300, 100, 30, 10, 3, 1, 0.3, 0.1 ng) and plotted against the Ct value (y-axis=Ct; x-axis=value, log scale) to generate a standard curve. Each unknown was assigned an arbitrary value based on the slope and y-intercept of the standard curve. The same process was carried out for TBP in order to use TBP values as a normalized template loaded into each reaction. The mean target value for each unknown was divided by the mean TBP value for each unknown to generate a normalized value for the target for each sample.

Method of RNA isolation from theca cells. Following treatment as indicated in serum free medium theca cells were flash frozen and stored at −80 C. Each 100 mm culture dish was harvested on ice in 500 µL trizol reagent (Sigma, St. Louis, Mo.). 100 µl of ultra pure chloroform was added to the trizol/cell mixture, vortexed for ten seconds, then centrifuged for 30 min at 14,000 rpm in a 4 C refrigerated Eppendorf Centrifuge (Hauppauge, N.Y.). The centrifuged samples were placed on ice and the upper phase was placed in a fresh RNase free eppendorf tube with an equivalent amount of ice cold ultrapure isopropropanol at −20 C overnight. The samples were then centrifuged for 30 min at 14,000 rpm in a 4 C refrigerated Eppendorf Centrifuge. The pellet was resuspended in 100 µl DEPC treated water, with 42 µL of 2M NaAC and 600 µL of ETOH then frozen at −80 C for 4-24 h. The samples were then centrifuged for 30 min at 14,000 rpm in a 4 C refrigerated Eppendorf Centrifuge (Hauppauge, N.Y.), rinsed with 70% ETOH, air dried, and resuspended in 50 µl of DEPC on ice. RNA was quantitated using a spectrophotometer at 260/280 or on a NanoDrop device. Samples usually have a 260/280 ratio above 1.60. CYP17, DENND1A.V2 and DENND1.V1 mRNA abundance were quantitated as described by quantitative Real-Time PCR using the Agilent One Step Brilliant III Kit, and normalized by TBP or 5S abundance.

Method of Measurement of Androgen/DHEA Biosynthesis. Following treatment of theca cells in 6-well culture plate as described in serum free medium the medium was collected and frozen and stored at −20 C. Each of treated 6-wells was rinsed with PBS, trypsinized, and counted twice with a Beckman Z2 Coulter Counter, Brea Calif. DHEA accumulation into the medium was quantitated using an ELISA platform (DRG International Incorporated, Springfield, N.J.).

Methodology for Western Analysis of DENND1A Protein in Normal and PCOS Theca Cells. To examine and compare DENND1A protein was examined in normal and PCOS theca cells, fourth passage theca cells were grown until subconfluent and transferred into serum free medium with and without forskolin for 24 hours. Following treatment, for whole cell lysates, theca cells were harvested in ice cold modified RIPA buffer (30 mM Tris, 150 mM NaCL, 50 mM Na F, 0.5 mM EDTA, 0.5% deoxycholic acid, 1.0% Nonident P-40, 0.1% SDS) containing 1 mM sodium orthovanadate, 0.5 mM phenymethylsufonyl fluoride, 1 mM dithiothreitol, 1.0 mM benzamidine, 1 µM microcystin, 2 µg/ml leupeptin, and 2 µg/ml pepstatin A. For isolation of nuclear extracts, cells were harvested with trypsin/EDTA and cytoplasmic extracts were prepared in buffer containing 0.1% NP-40, 20 mM HEPES (pH 7.9), 20 mM sodium chloride. The nuclear pellet was centrifuged at 10,000 g for 5 min, and nuclear extracts were prepared in buffer containing 20 mM HEPES, 25% glycerol, 500 mM sodium chloride, 1.5 mM magnesium chloride. Both buffers also contained 1 mM dithiothreitol, 0.5 mM PMSF, 0.2 mM EDTA, 2 µg/mL leupeptin, 1 mM benzamidine, 1 mM sodium orthovanadate, and 20 mM sodium fluoride to inhibit protein phosphatases and proteases. Protein concentrations of whole cell extracts (WCE) determined using a Bio-Rad DC protein assay (Hercules, Calif.). Protein samples of nuclear extracts (NE) were separated on a 10% SDS-PAGE, transferred to PVDF membrane, and Western analysis was performed using Abcam antibody specific for the N-terminal sequence of DENND1A, and was visualized using ECL (Pierce). From the results of these experiments we expected bands at approximately 110 kD, corresponding to DENND1A Variant 1, and an approximate 62 kD corresponding to DENND1A Variant 2, given that the N-terminal antibody purchased is to the common N-terminal peptide, PGVSVHLSVHSYFTVP-DTRELPSIPENRNLTEYFVAVDVNNMLHLYASML (SEQ ID NO:27) sequence that begins amino acid #13 of both DENND1A Variant 1 and 2 peptides.

Method for Isolation of Urine Exosomal mRNA. Exosomes are small vesicles of about 40-100 nm originating from within multi-vesicular bodies, that are secreted from cells into extra-cellular fluid, and are found in different bodily fluids such blood, blood derivatives, urine, and amniotic fluid. Exosomes are produced by all cell types, and have a molecular phenotype which largely reflects that of the parent cell. Their contents reflect the origin and the physiological status of the source cells, and thus exosomal RNAs can serve as biomarkers for various diseases.

Urine samples were obtained from normal women and women with PCOS, using the same clinical criteria described above, following informed consent under an IRB protocol approved by the Institutional Review Board of the Pennsylvania State University College of Medicine. The urine samples were collected and placed at 4 C until processed. The urine samples were then aliquoted into 15 ml tubes and centrifuged in a swing bucket in a Sorvall Super T21 Table Top Centrifuge at 300 g at 4 C for 10 minutes to remove particulate matter. The supernatant was transferred to a new tube and centrifuged at 2000 g 4 C for 10 minutes in the same centrifuge to clear cellular debris. The supernatant was transferred to a 17×100 mm culture tube and centrifuged at 12,000 g at 4 C for 30 minutes using a floor Beckman Coulter Avanti J-E Centrifuge. The supernatant was then transferred to 15 ml tube, and the sample was either frozen at −80 C until use, or exosomal RNA was extracted using a modified protocol of the "Urine Exosome RNA Isolation Kit" from Norgen (Thorold, CAN).

Using the Norgen Kit, 10 ml of the centrifuged urine was added to a fresh 15 cc conical tube on ice. 300 μl of Solution A1 and 250 μl of Solution A2 was added to each tube. The tubes were vortexed well for 10 seconds. Using the table top Sorvall Centrifuge, the tubes/samples were spun at 3200 rpm 4 C for 2 minutes. The supernatant was aspirated off, and the tubes/pellets were placed on ice. The pellet was resuspended in 300 μl of Solution B, and incubated at room temperature for 5 minutes, and on ice for 10 minutes. 300 μl of ice cold 67% Isopropanol was added to the mixture, and vortexed well for 10 seconds. The lysate was transferred to a mini filter spin column, provided by the kit with a collection tube. The lysate/column was spun in a table top microfuge at 14,000 rpm 4 C for 1 minute, and the flow through was discarded. 400 μl ice cold Wash Solution was added to the reassembled spin column, and centrifuged again at 14,000 rpm 4 C for 1 minute. The flow through was discarded, another 400 μl Wash Solution was applied and spun again at 14,000 rpm 4 C for 1 minute. The flow through was discarded, 400 μl Wash solution was applied (3 total washes) and spun at 14,000 rpm 4 C for 4 minutes. The collection tube with the flow through was discarded, and the spin column was placed in an elution tube. 50 μl of sterile dH$_2$O was added to the spin column and spun at 2,000 rpm 4 C for 2 minutes, followed by a 14,000 rpm 4 C spin for 2 minutes. Another 50 μl sterile dH$_2$O was added to the spin column, and again spun at 2,000 rpm 4 C for 2 minutes, followed by a 14,000 rpm 4 C spin for 2 minutes. The spin columns were discarded; the elution tubes were capped and spun a final time at 14,000 rpm 4 C for 10 minutes to pellet any remaining resin from the column. The supernatant/RNA was then transferred to new 1.5 ml tubes. Nucleic acid content was quantitated using a NanoDrop Spectrophotometer, the samples were then aliquoted into the desired ng/μl and frozen at −80 C.

While the invention has been described through specific embodiments, routine modifications will be apparent to those skilled in the art and such modifications are intended to be within the scope of the present invention.

What is claimed is:

1. A method for polycystic ovary syndrome diagnosis, the method comprising the steps of:
measuring an amount of DENND1A Variant 2 mRNA in a urine sample from a subject,
wherein the amount of DENND1A Variant 2 mRNA is measured by hybridizing a labeled probe to the DENND1A Variant 2 mRNA or to DNA amplified from the DENND1A Variant 2 mRNA, and detecting the labeled probe hybridized to the DENND1A Variant 2 mRNA or detecting the labeled probe hybridized to amplified DNA,
wherein said labeled probe hybridizes to a DENND1A Variant 2 mRNA or DNA sequence that is absent from DENND1A Variant 1 mRNA or DNA sequence; or
wherein the amount of DENND1A Variant 2 mRNA is measured by detecting a signal from a fluorescently labeled nucleotide released from a probe hybridized to amplified DNA, wherein the fluorescently labeled nucleotide is released by exonuclease activity on the probe during amplification of the DENND1A Variant 2 mRNA into double stranded DNA,
wherein said probe hybridizes to a DENND1A Variant 2 mRNA or DNA sequence that is absent from DENND1A Variant 1 mRNA or DNA sequence;
comparing the amount of DENND1A Variant 2 mRNA to a reference value; and
diagnosing said subject with polycystic ovary syndrome when said amount of DENND1A Variant 2 mRNA is increased as compared to the reference value.

2. The method of claim 1, wherein the measuring of the DENND1A Variant 2 mRNA comprises using a polymerase chain reaction to amplify the DENND1A Variant 2 mRNA into double stranded DNA.

3. The method of claim 1, wherein the urine sample from the subject comprises exosomes, wherein the exosomes comprise the DENND1A Variant 2 mRNA.

4. A method for selecting an individual as a candidate for therapy for polycystic ovary syndrome, the method comprising the steps of:
measuring an amount of DENND1A Variant 2 mRNA in a urine sample from said individual,
wherein the amount of DENND1A Variant 2 mRNA is measured by hybridizing a labeled probe to the DENND1A Variant 2 mRNA or to DNA amplified from the DENND1A Variant 2 mRNA, and detecting the labeled probe hybridized to the DENND1A Variant 2 mRNA or detecting the labeled probe hybridized to amplified DNA,
wherein said labeled probe hybridizes to a DENND1A Variant 2 mRNA or DNA sequence that is absent from DENND1A Variant 1 mRNA or DNA sequence; or
wherein the amount of DENND1A Variant 2 mRNA is measured by detecting a signal from a fluorescently labeled nucleotide released from a probe hybridized to amplified DNA, wherein the fluorescently labeled nucleotide is released by exonuclease activity on the probe during amplification of the DENND1A Variant 2 mRNA into double stranded DNA,
wherein said probe hybridizes to a DENND1A Variant 2 mRNA or DNA sequence that is absent from DENND1A Variant 1 mRNA or DNA sequence;
comparing the amount of DENND1A Variant 2 mRNA to a reference value, and
diagnosing said individual with polycystic ovary syndrome when said amount of DENND1A Variant 2 mRNA is increased as compared to the reference value, and
designating the individual diagnosed with polycystic ovary syndrome as a candidate for the polycystic ovary syndrome therapy.

5. The method of claim 1, wherein said DENND1A Variant 2 mRNA or DNA sequence encodes at least 15 contiguous amino acids of SEQ ID NO: 10.

6. The method of claim 5, wherein said DENND1A Variant 2 mRNA sequence encodes at least SEQ ID NO: 10.

7. The method of claim 6, wherein said DENND1A Variant 2 mRNA sequence encodes at least SEQ ID NO: 11.

8. The method of claim 4, wherein said DENND1A Variant 2 mRNA or DNA sequence encodes at least 15 contiguous amino acids of SEQ ID NO: 10.

9. The method of claim 8, wherein said DENND1A Variant 2 mRNA sequence encodes at least SEQ ID NO: 10.

10. The method of claim 9, wherein said DENND1A Variant 2 mRNA sequence encodes at least SEQ ID NO: 11.

11. A method of detecting DENND1A Variant 2 mRNA in a urine sample, the method comprising the steps of:
detecting whether DENND1A Variant 2 mRNA is present in a urine sample by contacting said urine sample with a probe that hybridizes to a DENND1A Variant 2 mRNA sequence and detecting binding between the probe and the DENND1A Variant 2 mRNA sequence, wherein the DENND1A Variant 2 mRNA sequence is absent in a DENND1A Variant 1 mRNA.

12. The method of claim 11, wherein said DENND1A Variant 2 mRNA sequence encodes at least fifteen contiguous amino acids of SEQ ID NO: 10.

13. The method of claim 12, wherein said DENND1A Variant 2 mRNA sequence encodes at least SEQ ID NO: 10.

14. The method of claim 13, wherein said DENND1A Variant 2 mRNA sequence encodes at least SEQ ID NO: 11.

* * * * *